US009995662B2

(12) United States Patent
Husain et al.

(10) Patent No.: US 9,995,662 B2
(45) Date of Patent: Jun. 12, 2018

(54) SINGLE CELL CAPTURE WITH POLYMER CAPTURE FILMS

(71) Applicant: WaferGen, Inc., Fremont, CA (US)

(72) Inventors: Syed A. Husain, Fremont, CA (US); Bradley L. Griswold, Fremont, CA (US); Michael Slater, Fremont, CA (US); Patricio Espinoza, Fremont, CA (US); Jude Dunne, Fremont, CA (US); Glenn Hein, Fremont, CA (US); Maithreyan Srinivasan, Fremont, CA (US)

(73) Assignee: TAKARA BIO USA, INC., Mountain View, CA (US)

(*) Notice: Subject to any disclaimer, the term of this patent is extended or adjusted under 35 U.S.C. 154(b) by 0 days. days.

(21) Appl. No.: 14/876,365

(22) Filed: Oct. 6, 2015

(65) Prior Publication Data
US 2016/0033378 A1 Feb. 4, 2016

Related U.S. Application Data

(63) Continuation of application No. 14/735,514, filed on Jun. 10, 2015, now abandoned.

(60) Provisional application No. 62/011,267, filed on Jun. 12, 2014, provisional application No. 62/086,044, filed on Dec. 1, 2014.

(51) Int. Cl.
*G01N 1/40* (2006.01)
*B01L 3/00* (2006.01)

(52) U.S. Cl.
CPC .......... *G01N 1/405* (2013.01); *B01L 3/50857* (2013.01); *B01L 3/502761* (2013.01); *B01L 2200/025* (2013.01); *B01L 2200/0668* (2013.01); *B01L 2300/0861* (2013.01); *B01L 2300/0893* (2013.01); *B01L 2300/165* (2013.01); *B01L 2400/049* (2013.01)

(58) Field of Classification Search
CPC ............... G01N 1/405; B01L 3/502761; B01L 3/50857; B01L 2200/025; B01L 2300/0861; B01L 2300/0893; B01L 2300/165; B01L 2400/049
See application file for complete search history.

(56) References Cited

U.S. PATENT DOCUMENTS

| 5,262,128 | A | 11/1993 | Leighton et al. | |
|---|---|---|---|---|
| 6,169,394 | B1 | 1/2001 | Fraizer et al. | |
| 6,322,683 | B1* | 11/2001 | Wolk | B01L 3/502707 204/600 |
| 6,984,297 | B2 | 1/2006 | Nisch et al. | |
| 6,989,089 | B2 | 1/2006 | Nisch et al. | |
| 7,192,752 | B2 | 3/2007 | Xu et al. | |
| 7,547,556 | B2 | 6/2009 | Hunter et al. | |
| 7,833,709 | B2 | 11/2010 | Joseph et al. | |
| 8,252,581 | B2 | 8/2012 | Joseph et al. | |
| 8,481,292 | B2 | 7/2013 | Casbon et al. | |
| 8,835,358 | B2 | 9/2014 | Fodor et al. | |
| 2002/0063067 | A1 | 5/2002 | Bech et al. | |
| 2002/0064841 | A1 | 5/2002 | Klemic et al. | |
| 2002/0146836 | A1 | 10/2002 | Neilson et al. | |
| 2003/0129646 | A1* | 7/2003 | Briscoe | F04B 19/006 435/6.19 |
| 2004/0115614 | A1 | 6/2004 | Burnett et al. | |
| 2005/0266478 | A1 | 12/2005 | Huang et al. | |
| 2006/0129043 | A1 | 6/2006 | Ben-Jacob et al. | |
| 2006/0166351 | A1* | 7/2006 | Harada | C12M 35/00 435/287.1 |
| 2006/0194255 | A1 | 8/2006 | Finkel | |
| 2007/0020640 | A1 | 1/2007 | McCloskey et al. | |
| 2007/0026382 | A1 | 2/2007 | Lynes et al. | |
| 2007/0243523 | A1* | 10/2007 | Ionescu-Zanetti | B01L 3/502715 435/4 |
| 2008/0199362 | A1 | 8/2008 | Chong et al. | |
| 2009/0061513 | A1 | 3/2009 | Andersson Svahn et al. | |

(Continued)

FOREIGN PATENT DOCUMENTS

WO      WO 9105519      5/1991
WO      WO 2013/130714 A1      9/2013
(Continued)

OTHER PUBLICATIONS

Barbier et al. "Stable Modification of PDMS Surface Properties by Plasma Polymerization: Application to the Formation of Double Emulsions in Microfluidic Systems." Langmuir. Jun. 6, 2006;22(12):5230-2.*
Zhu et al. "Microfluidic single-cell cultivation chip with controllable immobilization and selective release of yeast cells.."Lab Chip. Mar. 7, 2012;12(5):906-15.*
Ahmad et al. "A robotics platform for automated batch fabrication of high density, microfluidics-based DNA microarrays, with applications to single cell, multiplex assays of secreted proteins.."Rev Sci Instrum. Sep. 2011;82(9):094301.*
Chen et al. "Photolithographic surface micromachining of polydimethylsiloxane (PDMS)." Lab Chip. Jan. 21, 2012;12(2):391-5.*

(Continued)

*Primary Examiner* — Titilayo Moloye
(74) *Attorney, Agent, or Firm* — Bozicevic, Field & Francis LLP; Otto C. Guedelhoefer, IV; Bret E. Field

(57) ABSTRACT

The present invention provides methods, systems, assemblies, and articles for capturing single cells with a polymer capture film. In certain embodiments, the polymer capture films comprise a plurality of individual channels with top and bottom openings, where the channels are dimensioned such that a single cell is: i) is captured inside the channel, partially or substantially occluding the channel, when negative pressure is provided to the bottom opening; or ii) is captured by the top opening, but does not enter the channel, when negative pressure is provided to the bottom opening. In some embodiments, the channels of the polymer capture film align with the wells of a multi-well chip such that the cell, or the contents of the single cell, may be transferred to a corresponding well.

17 Claims, 10 Drawing Sheets

(56) References Cited

U.S. PATENT DOCUMENTS

| | | | |
|---|---|---|---|
| 2009/0098541 A1* | 4/2009 | Southern | B01L 3/502753 435/6.11 |
| 2009/0305901 A1* | 12/2009 | Seemann | B01F 5/064 506/7 |
| 2010/0183481 A1* | 7/2010 | Facer | B01J 19/0093 422/504 |
| 2011/0143964 A1 | 6/2011 | Zhou et al. | |
| 2011/0195496 A1* | 8/2011 | Muraguchi | G01N 33/54366 435/325 |
| 2011/0237445 A1* | 9/2011 | Andersson Svahn | C12Q 1/686 506/7 |
| 2011/0251102 A1 | 10/2011 | Osipchuk et al. | |
| 2012/0010091 A1 | 1/2012 | Linnarson | |
| 2012/0082985 A1* | 4/2012 | Zenhausern | B01L 3/5027 435/6.12 |
| 2012/0107912 A1* | 5/2012 | Hwang | C12M 47/06 435/235.1 |
| 2012/0182609 A1* | 7/2012 | Borenstein | B01L 3/502707 359/368 |
| 2013/0122539 A1* | 5/2013 | Li | B01D 67/0062 435/34 |
| 2013/0317130 A1* | 11/2013 | Brassard | B29C 43/021 521/146 |
| 2013/0337500 A1 | 12/2013 | Tan et al. | |
| 2015/0360226 A1 | 12/2015 | Husain et al. | |
| 2016/0045884 A1 | 2/2016 | Husain et al. | |

FOREIGN PATENT DOCUMENTS

| | | |
|---|---|---|
| WO | WO 2013180567 | 12/2013 |
| WO | WO 2015191684 | 12/2015 |

OTHER PUBLICATIONS

Sasuga et al. "Single-cell chemical lysis method for analyses of intracellular molecules using an array of picoliter-scale microwells." Anal Chem. Dec. 1, 2008;80(23):9141-9. (Year: 2008).*

Liu et al. "Microfabricated glass devices for rapid single cell immobilization in mouse zygote microinjection." Biomed Microdevices. Dec. 2009;11(6):1169-74 (Year: 2009).*

Bontoux et al., Integrating whole transcriptome assays on a lab-on-a-chip for single cell gene profiling, Lab Chip, 2008, 8:443-450.

Cheung et al., Microfluidic Impedance-Based Flow Cytometry, Cytometry Part A, 2010, 77A:648-666.

Chung et al., Highly Efficient Single Cell Capturing in Microwell Array Using Hydrodynamic Guiding Structures, Twelfth International Conference on Miniaturized Miniaturized Systems for Chemistry and Life Sciences Oct. 12-16, 2008, San Diego, California, USA, pp. 477-479.

Craig et al., Identification of genetic variants using bar-coded multiplexed sequencing, Nat. Methods, 2008, 5(10):887-893.

Duqi, Continuous Flow Single Cell Separation into Open Microwell Arrays, Ph.D. Dissertation, Alma Mater Studiorum-University of Bologna, 2012, 151 pages.

Esumi et al., Method for single-cell microarray analysis and application to gene-expression profiling of GABAergic neuron progenitors, Neuro. Res., 2008, 60:439-451.

Graham et al., The Coulter Principle: Foundation of an Industry, JALA, 2003, 8:72-81.

Hollas and Schuler, A Stochastic Approach to Count RNA Molecules Using DNA Sequencing Methods, Lecture Notes in Computer Science, Algorithms in Bioinformatics, vol. 2812, 2003, pp. 55-62.

Hosokawa et al., High-Density Microcavity Array for Cell Detection: Single-Cell Analysis of Hematopoietic Stem Cells in Peripheral Blood Mononuclear Cells, Anal. Chem., 2009, 81:5308-5313.

Hosokawa et al., Size-Based Isolation of Circulating Tumor Cells in Lung Cancer Patients Using a Microcavity Array System, PLoS One, 2013, 8:e67466.

Hug et al., Measurement of the number Of molecules of a single mRNA species in a complex mRNA preparation, J. Theor. Biol., 2003, 221:615-624.

Parameswaran et al., A pyrosequencing-tailored nucleotide barcode design unveils opportunities for large-scale sample multiplexing, Nucleic Acids Res. 2007, 35(19): e130.

Qui et al., DNA Sequence-Based "Bar Codes" for Tracking the Origins of Expressed Sequence Tags from a Maize cDNA Library Constructed Using Multiple mRNA Sources, Plant. Physiol., 133:475-481, 2003.

Revzin et al., Development of a microfabricated cytometry platform for characterization and sorting of individual leukocytes, Lab Chip, 2005, 5:30-37.

Sun and Morgan, Single-cell microfluidic impedance cytometry: a review, Microfluid Nanofluid, 2010, 8:423-443.

Sutcliffe et al., TOGA: An automated parsing technology for analyzing expression of nearly all genes, PNAS, 2000, 97(5):1976-1981.

Taguchi et al., Detection of Cryptosporidium parvum Oocysts Using a Microfluidic Device Equipped With the SUS Micromesh and FITC-Labeled Antibody, Biotech and Bioeng, 2007, 96:272-280.

International Search Report and Written Opinion for PCT/US2015/035060, dated Aug. 31, 2015, 10 pages.

Bodas et al. "Hydrophilization and hydrophobic recovery of PDMS by oxygen plasma and chemical treatment—An SEM investigation," Sensors and Actuators B: Chemical 123 (2007): 368-373.

Jen et al. "Single-Cell Chemical Lysis on Microftuidic Chips with Arrays of Microwells," Sensors 2012, vol. 12, pp. 347-358.

* cited by examiner

SINGLE CELL CAPTURE WITH POLYMER CAPTURE FILMS

The present application is a continuation of U.S. application Ser. No. 14/735,514 filed Jun. 10, 2015, which claims priority to U.S. Provisional application 62/011,267, filed Jun. 12, 2014 and U.S. Provisional application 62/086,044, filed Dec. 1, 2014, each of which are herein incorporated by reference in their entireties.

FIELD OF THE INVENTION

The present invention provides methods, systems, assemblies, and articles for capturing single cells with a polymer capture film. In certain embodiments, the polymer capture films comprise a plurality of individual channels with top and bottom openings, where the channels are dimensioned such that a single cell is: i) is captured inside the channel, partially or substantially occluding the channel, when negative pressure is provided to the bottom opening; or ii) is captured by the top opening, but does not enter the channel, when negative pressure is provided to the bottom opening. In some embodiments, the channels of the polymer capture film align with the wells of a multi-well chip such that the cell, or the contents of the single cell, may be transferred to a corresponding well.

BACKGROUND

Geneticists are striving to characterize complex diseases like cancer, autoimmune and neurological disorders, but finding the underlying mechanisms driving these diseases has been elusive. Somatic mutations, spontaneous variants that accumulate in cells over a lifetime, are a major factor that drives disease onset and reoccurrence. As cells accumulate new mutations, they form polyclonal cell populations that co-exist with normal cells. Sequencing bulk cell populations can mask the underlying heterogeneity of these unique rare cell types, making it difficult to distinguish them from normal germline mutations. The best way to reveal these differences and visualize the clonal architecture is to sequence individual cells in the population. While single-cell sequencing can help uncover mechanisms of complex disease, traditional approaches are expensive, labor intensive, and require large sample input. What is needed are methods to isolate single cells that, for example, are amenable for use with multi-well devices.

SUMMARY OF THE INVENTION

The present invention provides methods, systems, assemblies, and articles for capturing single cells with a polymer capture film. In certain embodiments, the polymer capture films comprise a plurality of individual channels with top and bottom openings, where the channels are dimensioned such that a single cell is: i) is captured inside the channel, partially or substantially occluding the channel, when negative pressure is provided to the bottom opening; or ii) is captured by the top opening, but does not enter the channel, when negative pressure is provided to the bottom opening. In some embodiments, the channels of the polymer capture film align with the wells of a multi-well chip such that the cell, or the contents of the single cell, may be transferred to a corresponding well.

In certain embodiments, the present invention provides methods, systems, assemblies, and articles for capturing single cells by individual channels or spots on a polymer film. In certain embodiments, the polymer films have a plurality of individual channels (e.g., in a multi-well matching pattern) that are able to capture single cells using particular sizes and negative pressure. In other embodiments, the polymer films have a plurality of individual hydrophilic spots (e.g., in a multi-well matching pattern) that are able to capture single cells. In certain embodiments, such polymer films, with captured single cells in a multi-well matching pattern, are mated with a multi-well plate or multi-well chip with a matching well opening pattern such that the captured cells can be dispensed therein, allowing each well to receive a single cell (e.g., which can then be lysed and the nucleic acid sequenced). In certain embodiments, a size-exclusion polymer film is employed that is, for example, attached to (e.g., by double-sided PCR compatible adhesive), and aligned with, a multi-well device. In some embodiments, multi-well through-devices are provided with cell-sized top openings and larger bottom openings (e.g., configured to receive reaction components). In other embodiments, a multi-well device is created by attaching a PCR compatible film to the bottom of a multi-well through-hole chip. In further embodiments, provided herein are capture chips with cell-sized dimples or wells (e.g., each containing a single cell), which can be mated with a multi-well device with a plurality of wells containing reagents that will detach and/or lysis the single cells. The capture chips and multi-well devices can be mated such that the dimples of the chip and wells of the device are aligned, and then treated such that reagents flow from the wells of the multi-well device to cells in the cell-sized dimples, and then treated again such that the treated cells flow into the well of the multi-well device.

In some embodiments, provided herein are articles of manufacture comprising a polymer film, wherein the polymer film comprises a top surface, a bottom surface, and a plurality of individual channels extending through the polymer film (e.g., arranged in a multi-well device pattern), wherein each of the individual channels: a) has a top opening in the top surface of the polymer film, b) has a bottom opening in the bottom surface of the polymer film, and c) is dimensioned such that one cell, and only the one cell, from a cell suspension: i) is captured inside the individual channel, partially or substantially occluding the individual channel, when negative pressure is provided to the bottom opening; or ii) is captured by the top opening, but does not enter the individual channel, when negative pressure is provided to the bottom opening. In particular embodiments, the top openings of the plurality of individual channels matches one-for-one, and aligns with, the well openings in a multi-well device (e.g., multi-well plate or multi-well chip).

In particular embodiments, provided herein are systems or assemblies comprising: a) a polymer film comprising a top surface, a bottom surface, and a plurality of individual channels extending through the polymer film, wherein each of the individual channels: i) has a top opening in the top surface of the polymer film, ii) has a bottom opening in the bottom surface of the polymer film, and iii) is dimensioned such that one cell, and only the one cell, from a cell suspension: A) is captured inside the individual channel, partially or substantially occluding the individual channel, when negative pressure is provided to the bottom opening; or B) is captured by the top opening, but does not enter the individual channel, when negative pressure is provided to the bottom opening; and b) a porous layer comprising a porous material that allows liquid, but not cells, to pass therethrough, wherein the porous layer is dimensioned to be contacted with the bottom surface of the polymer film such that the bottom opening of each of the plurality of individuals channels is covered by the porous material.

In further embodiments, provided herein are methods of isolating single cells comprising: a) contacting a cell suspension with a cell-isolating system, wherein the cell-isolating system comprises: i) a polymer film comprising a top surface, a bottom surface, and a plurality of individual channels extending through the polymer film, wherein each of the individual channels: A) has a top opening in the top surface of the polymer film, B) has a bottom opening in the bottom surface of the polymer film, and C) is dimensioned such that one cell, and only the one cell, from the cell suspension: 1) is captured inside the individual channel, partially or substantially occluding the individual channel, when negative pressure is provided to the bottom opening; or 2) is captured by the top opening, but does not enter the individual channel, when negative pressure is provided to the bottom opening; ii) a pneumatic device that provides the negative pressure, wherein the pneumatic device comprises an interface surface, and iii) a porous layer comprising a porous material that allows liquid, but not cells, to pass therethrough, wherein the porous layer is in contact with: A) the bottom surface of the polymer film such that the bottom opening of each of the plurality of individuals channels is covered by the porous material; and B) the interface surface of the pneumatic device; b) incubating the cell suspension with the cell-isolating system, wherein the pneumatic device provides the negative pressure, such that each of the individual channels in the polymer film captures one, and only one, cell from the cell suspension such that each individual channel has one captured cell; and c) washing the polymer film to remove non-captured cells from the cell suspension to generate a captured-cell polymer film.

In some embodiments, the methods further comprise bringing together the captured-cell polymer film and a multi-well device (e.g., multi-well plate or multi-well chip) to generate an assembly, wherein the multi-well device has a plurality of well-openings, and wherein the top openings of the plurality of individual channels of the captured-cells polymer film matches one-for-one, and aligns with, the plurality of well openings in the multi-well device. In particular embodiments, the methods further comprise the step of treating the assembly such that the one captured cell for each of the individual channels, or partial contents of the one captured cell for each of the individual channels, is transferred into the corresponding well openings of the multi-well device (e.g., multi-well plate or multi-well chip). In certain embodiments, the assembly is centrifuged to release the cells from the polymer to the multi-well device, or the negative pressure is stopped, and/or positive pressure is employed to release the cells.

In certain embodiments, the captured cells are lysed while still on the polymer, prior to being contacted with the multi-well device. In other embodiments, the methods further comprise the step of adding reagents to each of the well openings in the multi-well device such that the one captured cell, or contents of the one captured cell, are modified. In further embodiments, the reagents are selected from the group consisting of: a buffer, a lyse buffer, a polymerase, sequencing reagents, proteinase, and nucleotides. In particular embodiments, once a single cell is in each of the plurality of wells in the multi-well device, a user or an automated system (e.g., from WAFERGEN) dispenses a cocktail of nickase and a polymerase (e.g., Pyrophage 3137 polymerase) and a lyse buffer. The wells are then treated at about 37 degrees C., then 95 degrees C. to inactivate nickase, and isothermal amplification is performed by using the polymerase. In certain embodiments, the cells are alternatively thermally lysed. Proteinase (e.g., Proteinase K) is then dispensed into the wells, incubated at 55 degrees C. (to digest polymerase, such as pyrophage 3137), and the incubation at 95 degrees C. is conducted to inactivate the proteinase. Then, gene specific reactions can be conducted in each well.

In additional embodiments, the top openings of the plurality of individual channels matches one-for-one, and aligns with, the well openings in a multi-well device. In further embodiments, the plurality of individual channels comprises at least 50, at least 500, at least 5000, or at least 50,000 individual channels (e.g., at least 50 . . . 100 . . . 687 . . . 1000 . . . 5000 . . . 7500 . . . 13,000 . . . 33,000 . . . or 50,000 individual channels). In certain embodiments, the well openings in the multi-well device each have a diameter of about 50 µm to 900 µm (e.g., 50 . . . 100 . . . 300 . . . 500 . . . 700 . . . 900 um).

In some embodiments, the plurality of wells in the multi-well device comprises at least 50, at least 500, at least 5000, or at least 50,000 individual wells (e.g., at least 50 . . . 100 . . . 687 . . . 1000 . . . 5000 . . . 7500 . . . 13,000 . . . 33,000 . . . or 50,000 individual wells).

In further embodiments, the polymer film is composed of a hydrophobic polymer. In certain embodiments, the hydrophobic polymer comprises polyimide, polyester, polyethylene, polyurethane, TEFLON and/or PTFE (e.g., that are about 20-30 µm thick, with 3-5 µm holes). In other embodiments, the top surface of the polymer films comprises a hydrophobic coating. In particular embodiments, the hydrophobic coating comprises a material selected from the group consisting of: a polyacrylate (e.g., Poly(butyl acrylate), and Poly(methyl acrylate), Acrylonitrile Polymers and Copolymers (e.g., Polyacrylonitrile), Maleic Anhydride Copolymers (e.g., Poly(styrene-co-maleic anhydride)), Methacrylate Polymers (e.g., Poly(benzyl methacrylate) and Poly(butyl methacrylate)), Amides and Imides (e.g., nylon), Carbonates (e.g., Poly(Bisphenol A carbonate)), Dienes (e.g., Polybutadiene), Esters (e.g., Poly(1,4-butylene succinate)), Ethers (e.g., Poly(propylene glycol)), Fluorocarbons (e.g., Poly(tetrafluoroethylene)), fluorosilane, Olefins (e.g., Polyethylene), Styrenes (e.g., Polystyrene), Vinyl Acetals (e.g., Poly(vinyl butyral-co-vinyl alcohol-co-vinyl acetate)), Vinyl and Vinylidene Chlorides (e.g., Poly(vinyl chloride)), Vinyl Esters (e.g., Poly(vinyl acetate)), Vinyl Ethers and Ketones (e.g., Poly(ethyl vinyl ether)), Vinylpyridine and Vinypyrrolidone Polymers (e.g., Poly(4-vinylpyridine)), HYDROFOE coating from Lotus Leaf, and ACULON hydrophobic coatings.

In certain embodiments, the porous material is selected from the group consisting of: a rigid porous foam, ultra high molecular weight polyethylene (UHMWPE), high density polyethylene (HDPE), low density polyethylene (LDPE), very low density polyethylene (VLDPE), polypropylene (PP), ethylene vinyl acetate (EVA), polystyrene (PS), epoxy glass, and phenol glass. In other embodiments, the porous material is a material from GENPORE (Morgantown, RD), POREX (Fairburn, Ga.), or PERMAPLAS Corp. (Fayetteville, Ga.).

In additional embodiments, the top opening of each of the individual channels is about 5 µm to about 80 µm in diameter (e.g., 5 . . . 15 . . . 25 . . . 45 . . . 65 . . . or about 80 um). In certain embodiments, the individual channels are laser-formed channels (e.g., using UV laser drilled or CO2 or excimer laser drilled). In other embodiments, photolithography or plasma etching is used to generate the channels in the polymer film. In certain embodiments, the polymer film is about 1 square centimeter to about 16 square centimeters (e.g., 1 . . . 5 . . . 10 . . . 13 . . . or 16 square centimeters).

In certain embodiments, the systems further comprise a multi-well device (e.g., multi-well plate or multi-well chip), wherein the top openings of the plurality of individual channels matches one-for-one, and aligns with, the well openings in the multi-well device. In other embodiments, the polymer film has a thickness between 25 µm and 2 mm (e.g., 25 µm . . . 75 µm . . . 500 µm . . . 1 mm . . . 2 mm). In other embodiments, each of the plurality of individual channels is approximately cylindrical.

In some embodiments, the one cell for each of the individual channels is selected from the group consisting of: a platelet (about 2 µm diameter), a red blood cell (about 3 to 8 µm diameter), a neutrophil (about 8-10 µm diameter), a lymphocyte (about 6-12 µm diameter), an exocrine cell (about 10 µm diameter), a fibroblast (about 10-15 µm diameter), an osteocyte (about 10-20 µm diameter), a chondrocyte or a liver cell (about 20 µm diameter), a goblet or ciliated cell (about 50 µm long and 5-10 µm wide), a macrophage (about 20-80 µm diameter), a hematopoietic stem cell (about 30-40 µm diameter), an adipocyte filled with stored lipid (about 70-120 µm diameter), and a neuron (about 4-120 µm diameter). In certain embodiments, the cells are prokaryotic or eukaryotic. In some embodiments, the cells are mammalian cells (e.g., human cells).

In some embodiments, the systems further comprise c) a pneumatic device that provides the negative pressure, wherein the pneumatic device comprises an interface surface, and wherein the porous layer is dimensioned to be contacted with the interface surface of the pneumatic device. In other embodiments, the pneumatic device comprises a high precision gauge that allows a determination if all or substantially all of the individual channels are partially or substantially occluded by a cell. In other embodiments, the porous layer is contacted with the bottom surface of the polymer film and the interface surface of the pneumatic device. In particular embodiments, the pneumatic device is further configured to provide positive pressure sufficient to dislodge the one cell from each of the individual channels. In other embodiments, the cell suspension comprises between 100 and $1 \times 10^{13}$ cells (e.g., 100 . . . 1000 . . . $1 \times 10^6$ . . . $1 \times 10^9$ . . . $1 \times 10^{12}$ and $1 \times 10^{13}$).

In certain embodiments, provided herein are articles of manufacture comprising a polymer film, wherein the polymer film comprises a top surface, wherein the top surface is mostly or completely hydrophobic except for a plurality of individual hydrophilic spots arranged in a multi-well pattern, wherein each of the individual hydrophilic spots is sized such that one cell, and only the one cell, from a cell suspension is captured by each of the individual hydrophilic spots, and wherein the multi-well pattern matches one-for-one, and aligns with, the plurality of well openings in a multi-well device (e.g., multi-well plate or multi-well chip). In particular embodiments, the hydrophilic spots are composed of polydopamine or similar material (see, Kang and Choi, Bull. Korean, Soc., 2013, 34(8):2525-2527, herein incorporated by reference). In other embodiments, the individual hydrophilic spots are 5-30 µm (e.g., about 5 . . . 15 . . . 25 . . . or about 30 µm) in diameter.

In certain embodiments, provided herein are systems comprising: a) a multi-well device (e.g., multi-well plate or multi-well chip), wherein the multi-well device comprises a plurality of well openings, and b) a polymer film comprising a top surface, wherein the top surface is hydrophobic except for a plurality of individual hydrophilic spots arranged in a multi-well pattern, wherein each of the individual hydrophilic spots is sized such that one cell, and only the one cell, from a cell suspension is captured by each of the individual hydrophilic spots, and wherein the multi-well pattern matches one-for-one, and aligns with, the plurality of well openings in the multi-well device.

In particular embodiments, provided herein are methods comprising: a) contacting a cell suspension with a cell-isolating polymer film, wherein the cell-isolating polymer film comprises a top surface, wherein the top surface is hydrophobic except for a plurality of individual hydrophilic spots arranged in a multi-well pattern, wherein each of the individual hydrophilic spots is sized such that one cell, and only the one cell, from a cell suspension is captured by each of the individual hydrophilic spots, and wherein the multi-well pattern matches one-for-one, and aligns with, the plurality of well openings in a multi-well device (e.g., multi-well plate or multi-well chip); b) incubating the cell suspension with the cell-isolating polymer film such that each of the individual hydrophilic spots captures one, and only one, cell from the cell suspension such that each of the individual spots has one captured cell; and c) washing the cell-isolating polymer film to remove non-captured cells from the cell suspension to generate a captured-cell polymer film.

In additional embodiments, the methods further comprise bringing together the captured-cell polymer film and the multi-well device (e.g., multi-well plate or the multi-well chip) to generate an assembly, wherein the multi-well device has a plurality of well-openings, and wherein the individual hydrophilic spots (each with a captured cell) of the captured-cell polymer film matches one-for-one, and aligns with, the plurality of well openings in the multi-well device. In other embodiments, the methods further comprise the step of treating the assembly such that the one captured cell for each of the individual hydrophilic spots, or partial contents of the one captured cell for each of the individual hydrophilic spots, is transferred into the corresponding well openings of the multi-well device (e.g., plate or multi-well chip). For example, in certain embodiments, the assembly is centrifuged to transfer the cells, or buffer conditions are changed to allow the cells to release from the hydrophilic spots. In particular embodiments, the cells are lysed on the polymer film prior to being contacted with the multi-well device. In some embodiments, the methods further comprise the step of adding reagents to each of the well openings in the multi-well device such that the one captured cell, or contents of the one captured cell, are modified. In other embodiments, the reagents are selected from the group consisting of: a buffer, a lyse buffer, a polymerase, sequencing reagents, proteinase, and nucleotides.

In some embodiments, provided herein are systems comprising: a) a multi-well through-hole chip with a top surface and a bottom surface; and b) PCR compatible film which is attached to, or attachable to, said bottom surface of said multi-well through-hole chip to create a multi-well device with a plurality of wells, wherein said PCR compatible film forms the bottom of each of said plurality of wells. In particular embodiments, the systems further comprise a size-exclusion polymer film, wherein said size-exclusion polymer film is attached to said top surface of said multi-well through-hole chip.

In certain embodiments, provided herein are systems comprising: a) a multi-well device comprising a plurality of well openings; b) a polymer film comprising a top surface;

wherein said top surface is hydrophobic except for a plurality of individual hydrophilic spots arranged in a multi-well pattern, wherein each of said individual hydrophilic spots is sized such that one cell, and only said one cell, from a cell suspension is captured by each of said individual hydrophilic spots, and wherein said multi-well pattern matches one-for-one, and aligns with, said plurality of well openings in said multi-well device; and c) double sided PCR compatible adhesive, wherein said double-sided PCR compatible adhesive bonds said polymer film to said multi-well device.

In particular embodiments, the multi-well device is formed from a multi-well through-hole chip combined with PCR compatible film, wherein said PCR compatible film is attached to the bottom of said multi-well through-hole chip thereby creating a multi-well device with a plurality of wells, wherein said PCR compatible film forms the bottom of each of said plurality of wells.

In certain embodiments, provided herein are multi-well through chips comprising: a substrate with a plurality of through-holes therein, wherein each through-hole has a top opening and a bottom opening, wherein said top opening has a diameter that is sized to receive only a single cell, and wherein said bottom opening has a diameter that is larger than said top opening. In some embodiments, the diameter of the bottom opening is at least 10% larger than said top opening (e.g., 10% . . . 25% . . . 75% . . . 100% . . . 300% . . . 1000% or more). In additional embodiments, the substrate comprises silicon, quartz, glass, or any combination thereof. In further embodiments, the diameter of the top opening is 2 and 50 um (e.g., 2 . . . 24 . . . 40 um or 2-10 um, 2-20 um, 4-10; 10-25; and 25-50 um). In other embodiments, the diameter of said bottom opening is 100 to 800 um (e.g., 100 . . . 450 . . . 600 . . . or 800 um). In certain embodiments, the substrate has a thickness from 0.5 mm to 3.0 mm (e.g., 0.5 . . . 1.0 . . . 2.0 . . . 2.6 . . . 3.0 mm). In further embodiments, the substrate comprises a silicon wafer bonded to a glass wafer. In some embodiments, the top openings are in said silicon wafer and said bottom openings are in said glass wafer. In additional embodiments, the single cells are selected from the group consisting of: osteocyte, chondrocyte, nerve cell, epithelial cell, muscle cell, secretory cell, adipose cell, red blood cell, white blood cell, platelet, and thrombocyte.

In some embodiments, provided herein are methods comprising: a) contacting the multi-well through chip described herein with a solution containing cells, such that a single cell enters the top opening of at least some of said plurality of through-holes; b) applying a cover to the top openings of said at least some of said plurality of through-holes to create a multi-well device with a plurality of wells each containing a single cell, wherein the cover forms the bottom of each of said plurality of wells. In additional embodiments, the methods further comprise: adding reagents to at least some of the plurality of wells, wherein the reagents are useful for conducting a bio-chemical reaction. In other embodiments, the reagents comprise an agent selected from: a lysis buffer, PCR primers, polymerase, and combinations thereof. In additional embodiments, the cover comprises PCR compatible film.

In certain embodiments, provided herein are systems comprising: a) a capture chip comprising a substrate comprising a plurality of cell-sized dimples or wells that each allow a single cell to be captured from a cell mixture; and b) a multi-well chip device comprising a plurality of wells, wherein said plurality of cell-sized dimples or wells matches one-for-one, and aligns with, said plurality of wells in said multi-well chip.

In particular embodiments, some or all of said cell-sized dimples or well each contain a single cell. In some embodiments, some or all of said plurality of wells in said multi-well chip contain reagents that detach and/or lysis cells. In additional embodiments, some or all of said cell-sized dimples or well each contain a single cell. In further embodiments, the cell-sized dimples or wells are etched via photolithography.

In certain embodiments, provided herein are methods comprising: a) providing: i) a capture chip comprising a substrate comprising a plurality of cell-sized dimples or wells that each allow a single cell to be captured from a cell mixture, wherein each of said cell-sized dimples or wells contains a single cell; and ii) a multi-well chip device comprising a plurality of wells, wherein said plurality of cell-sized dimples or wells matches one-for-one, and aligns with, said plurality of wells in said multi-well chip, wherein each of said plurality of well contains reagents that detach and/or lyse cells; b) bringing together said capture chip and said multi-well chip to form a mated-device such that said cell-sized dimples or wells of said capture chip are aligned with said wells of said multi-well device; c) agitating said mated device such that said reagents in said wells of said multi-well device travel into said cell-sized dimples or wells, contacting said single cell to create a treated cell; and d) agitating said mated device such that treated cell in each of said cell-sized dimples or wells travels into the corresponding well of said multi-well device. In some embodiments, the agitating comprises providing a centrifugal force.

In particular embodiments, at least some of the plurality of wells in the multi-well devices have a volume between 0.1 nanoliters and 500 nanoliters (e.g., about 0.1 nl . . . 0.9 nl . . . 1.5 nl . . . 5.0 nl . . . 10 nl . . . 20 nl . . . 35 nl . . . 50 nl . . . 75 nl . . . 100 nl . . . 150 nl . . . 300 nl . . . 450 nl . . . 500 nl). In particular embodiments, at least some of the plurality of wells has a volume between 1.0 nanoliter and 250 nanoliters (e.g., 1-250 nl, 10-200 nl, 25-150 nl, 40-100 nl, or 50-100 nl). In some embodiments, the plurality of wells comprises at least 3 open wells (e.g., 3 . . . 10 . . . 100 . . . 350 . . . 500 . . . 750 . . . 1000 . . . 1500 . . . 3000 . . . 5000 . . . 7500 . . . 10,000 . . . 15,000 . . . 20,000 . . . 30,000 . . . 45,000 or more open wells).

In additional embodiments, the multi-well device (e.g., chip) has a length of 10 mm to 200 mm (e.g., 10 mm . . . 50 mm . . . 100 mm . . . 150 mm . . . or 200 mm), a width of 10 mm to 200 mm (e.g., 10 mm . . . 50 mm . . . 100 mm . . . 150 mm . . . or 200 mm), and a thickness of 0.1 mm to 10 centimeters (e.g., 0.1 mm . . . 1.0 mm . . . 10 mm . . . 10 cm). In other embodiments, the substrate used for the multi-well device comprises a material selected from the group consisting of: glass, ceramics, metalloids, silicon, a silicate, silicon nitride, silicon dioxide, quartz, gallium arsenide, a plastic, and an organic polymeric material. In additional embodiments, the multi-well device (e.g., chip) further comprises individually-controlled heating elements, each of which is operably coupled to a well.

In some embodiments, the present disclosure provides articles of manufacture comprising: a polymer capture film, wherein the polymer capture film comprises a top surface, a bottom surface, and a plurality of individual channels extending through the polymer capture film, wherein each of the individual channels: a) has a top opening in the top surface of the polymer capture film, b) has a bottom opening in the bottom surface of the polymer capture film, and c) is dimensioned such that one cell (e.g., and only the one cell), from a cell suspension: i) is captured inside the individual channel, partially or substantially occluding the individual channel, when negative pressure is provided to the bottom opening; or ii) is captured by the top opening, but does not enter the individual channel, when negative pressure is provided to the bottom opening.

In certain embodiments, the polymer capture film comprises an inert and/or a hydrophobic polymer (e.g., polyimide, polyester, polyethylene, polyurethane, TEFLON and/or PTFE). In further embodiments, the article further comprises at least one film guide component attached to, or integral with, the polymer capture film (e.g., flaps or other protrusions with guide holes therein) wherein the film guide component is configured to allow alignment of the plurality of individual channels in the polymer capture film one-for-one with wells in a multi-well device and/or holes in a polymer film support plate. In other embodiments, the top openings of the plurality of individual channels matches one-for-one, and aligns with, the well openings in a multi-well device (e.g., a SMARTCHIP from Wafergen Biosystems). In further embodiments, the plurality of individual channels comprises at least 10 . . . 250 . . . 500 . . . 1000 . . . 5000 . . . or 30,000 individual channels. In additional embodiments, each of the individual channels is dimensioned such that one cell (e.g., and only the one cell) from a cell suspension is captured by the top opening, but does not enter the individual channel, when negative pressure is provided to the bottom opening. In other embodiments, the polymer film has a thickness between 10 µm and 50 µm (e.g., 10 . . . 20 . . . 40 . . . or 50 µm), and wherein the top surface has an area between 1 cm$^2$ and 30 cm$^2$ (e.g., 1 . . . 20 . . . 25 . . . or 30 cm$^2$). In additional embodiments, each of the individual channels has a diameter of about 2-10 µm (e.g., 2 . . . 4 . . . 6 . . . 8 . . . 10 µm).

In certain embodiments, the present disclosure provides systems comprising: a) a polymer capture film comprising a top surface, a bottom surface, and a plurality of individual channels extending through the polymer capture film, wherein each of the individual channels: i) has a top opening in the top surface of the polymer capture film, ii) has a bottom opening in the bottom surface of the polymer capture film, and iii) is dimensioned such that one cell (e.g., and only the one cell) from a cell suspension: A) is captured inside the individual channel, partially or substantially occluding the individual channel, when negative pressure is provided to the bottom opening; or B) is captured by the top opening, but does not enter the individual channel, when negative pressure is provided to the bottom opening; and b) a first component selected from the group consisting of: i) a porous layer comprising a porous material that allows liquid, but not cells, to pass therethrough, wherein the porous layer is dimensioned to be contacted with the bottom surface of the polymer capture film such that the bottom opening of each of the plurality of individuals channels is covered by the porous material; ii) a film support component comprising a substrate (e.g., metal, ceramic, silicon, aluminum, etc.) with a plurality of individual holes therethrough (e.g., which are larger in diameter than the channels in the polymer capture film) which align one-for-one with the plurality of individual channels in the polymer capture film, wherein the film support component is dimensioned to be contacted with, and support, the bottom surface of the polymer capture film; iii) a multi-well chip comprising a plurality of individual wells (e.g., microwells or nanowells), wherein the multi-well chip is dimensioned to be contacted with the top surface of the polymer capture film such that the plurality of individual wells align one-for-one with the plurality of individual channels in the polymer capture film; and iv) a cell (e.g., viable cell) that: A) is captured inside one of the individual channels, or B) is captured by the top opening of one of the individual channels.

In certain embodiments, the systems further comprise a housing base, wherein the housing base is configured to contain (e.g., provide a bottom support for, and generally surround) the polymer capture film and comprises at least one base feature selected from the group consisting of: a vacuum connection port (e.g., in the bottom of the housing base), at least two guide pins for aligning the polymer capture film and the film support component, a film support plate recess, a liquid reservoir, a gasket, and at least one connection rod for connection to a housing top.

In particular embodiments, the systems further comprise a housing top, wherein the housing top is configured to connect to a housing base to enclose the polymer capture film and comprises at least one top feature selected from the group consisting of: an inlet port (to connect to sample delivery component to deliver cell suspensions and wash solutions), an outlet port (e.g., to connect to a diaphragm pump), a slot array (e.g., with a plurality of slots to guide liquid into the channels of the polymer capture film), a guide pin receiver, and a connection rod receiver.

In certain embodiments, the polymer capture film comprises an inert and/or hydrophobic polymer (e.g., polyimide, polyester, polyethylene, polyurethane, TEFLON PTFE, or combinations of any two, any three, any four, any five, or any six of such polymers). In particular embodiments, the polymer capture film is about 20-30 µm thick, with 3-5 µm holes. In further embodiments, the polymer capture film further comprises at least one film guide component attached to, or integral with, the polymer capture film, wherein the film guide component is configured to allow alignment of the plurality of individual channels in the polymer capture film one-for-one with the wells in the multi-well device and/or the holes in the polymer film support plate. In other embodiments, the top openings of the plurality of individual channels matches one-for-one, and aligns with, the well openings in the multi-well device and/or the holes in the polymer film support plate. In additional embodiments, the polymer capture film has at least one of the properties selected from the group consisting of: i) the plurality of individual channels comprises at least 5 . . . 100 . . . 500 . . . 30,000 individual channels, ii) each of the individual channels is dimensioned such that one cell, and only the one cell, from a cell suspension is captured by the top opening, but does not enter the individual channel, when negative pressure is provided to the bottom opening, iii) has a thickness between 10 µm and 50 µm, iv) the top surface has an area between 1 cm$^2$ and 30 cm$^2$; and iv) each of the individual channels has a diameter of about 2-120 µm.

In some embodiments, the cell is selected from the group consisting of: a platelet (about 2 µm diameter), a red blood cell (about 3 to 8 µm diameter), a neutrophil (about 8-10 µm diameter), a lymphocyte (about 6-12 µm diameter), an exocrine cell (about 10 µm diameter), a fibroblast (about 10-15 µm diameter), an osteocyte (about 10-20 µm diameter), a chondrocyte or a liver cell (about 20 µm diameter), a goblet or ciliated cell (about 50 µm long and 5-10 µm wide), a macrophage (about 20-80 µm diameter), a hematopoietic stem cell (about 30-40 µm diameter), an adipocyte filled with stored lipid (about 70-120 µm diameter), and a neuron (about 4-120 µm diameter). In other embodiments, the systems further comprise a second component selected from the group consisting of: a vacuum pump that provides the negative pressure, a centrifuge motor configured to spin a housing base, a diaphragm pump, a chip alignment component, a swing arm attached to a swing arm support rod, a sample delivery component, a user interface display, and at least one waste container.

In some embodiments, the present disclosure provides methods of isolating single cells comprising: a) contacting a cell suspension with a cell-isolating system, wherein the cell-isolating system comprises: i) a polymer capture film comprising a top surface, a bottom surface, and a plurality of individual channels extending through the polymer capture film, wherein each of the individual channels: A) has a top opening in the top surface of the polymer capture film, B) has a bottom opening in the bottom surface of the polymer capture film, and C) is dimensioned such that one cell, and only the one cell, from the cell suspension: 1) is captured inside the individual channel, partially or substantially occluding the individual channel, when negative pressure is provided to the bottom opening; or 2) is captured by the top opening, but does not enter the individual channel, when negative pressure is provided to the bottom opening; and ii) a pneumatic device that provides the negative pressure, and b) incubating the cell suspension with the cell-isolating system, wherein the pneumatic device provides the negative pressure, such that at least some of the individual channels in the polymer captures film captures one cell from the cell suspension such that at least some of the plurality of individual channels has one captured cell; and c) washing the polymer capture film to remove non-captured cells to generate a captured-cell polymer film.

In other embodiments, the method further comprises bringing together the captured-cell polymer film and a multi-well device to generate an assembly, wherein the multi-well device has a plurality of well-openings, and wherein the top openings of the plurality of individual channels of the captured-cells polymer film matches one-for-one, and aligns with, the plurality of well openings in the multi-well device. In certain embodiments, the cell isolating system further comprises: i) a porous layer comprising a porous material that allows liquid, but not cells, to pass therethrough, wherein the porous layer is dimensioned to be contacted with the bottom surface of the polymer capture film such that the bottom opening of each of the plurality of individuals channels is covered by the porous material; or ii) a film support component comprising a substrate with a plurality of individual holes therethrough which align one-for-one with the plurality of individual channels in the polymer capture film, wherein the film support component is dimensioned to be contacted with, and support, the bottom surface of the polymer capture film.

DETAILED DESCRIPTION

Figure 1A:
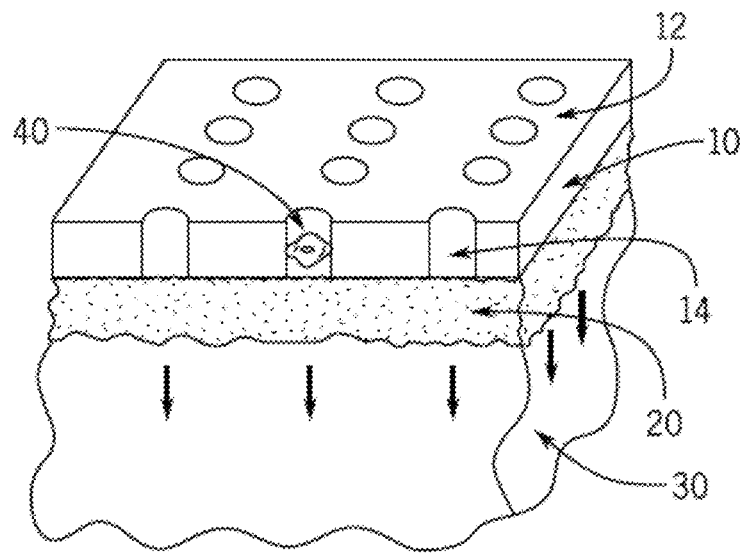
FIG. 1A shows an exemplary system or assembly of the present invention, including a polymer film (10) with a top surface (12) and plurality of channels (one channel is labeled with 14). The polymer film (10) is sitting on a porous layer (20), which itself is sitting on a pneumatic device (30) that provides negative pressure (shown by down arrows) to the bottom of the channels (14). A channel (14) is shown with a cell (40) inside that is substantially occluding the channel.

The present invention provides methods, systems, assemblies, and articles for capturing single cells with a polymer capture film. In certain embodiments, the polymer capture films comprise a plurality of individual channels with top and bottom openings, where the channels are dimensioned such that a single cell is: i) is captured inside the channel, partially or substantially occluding the channel, when negative pressure is provided to the bottom opening; or ii) is captured by the top opening, but does not enter the channel, when negative pressure is provided to the bottom opening. In some embodiments, the channels of the polymer capture film align with the wells of a multi-well chip such that the cell, or the contents of the single cell, may be transferred to a corresponding well.

In certain embodiments, present invention provides methods, systems, assemblies, and articles for capturing single cells by individual channels or spots on a polymer film. In certain embodiments, the polymer films have a plurality of individual channels (e.g., in a multi-well matching pattern) that are able to capture single cells using particular sizes and negative pressure. In other embodiments, the polymer films have a plurality of individual hydrophilic spots (e.g., in a multi-well matching pattern) that are able to capture single cells. In certain embodiments, such polymer films, with captured single cells in a multi-well matching pattern, are mated with a multi-well device with a matching well opening pattern such that the captured cells can be dispensed therein, allowing each well to receive a single cell (e.g., which can then be lysed and the nucleic acid sequenced). In certain embodiments, a size-exclusion polymer film is employed that is, for example, attached to (e.g., by double-sided PCR compatible adhesive), and aligned with, a multi-well device. In some embodiments, multi-well through-devices are provided with cell-sized top openings and larger bottom openings (e.g., configured to receive reaction components). In other embodiments, a multi-well device is created by attaching a PCR compatible film to the bottom of a multi-well through-hole chip. In further embodiments, provided herein are capture chips with cell-sized dimples or wells (e.g., each containing a single cell), which can be mated with a multi-well device with a plurality of wells containing reagents that will detach and/or lysis the single cells. The capture chips and multi-well devices can be mated such that the dimples of the chip and wells of the device are aligned, and then treated such that reagents flow from the wells of the multi-well device to cells in the cell-sized dimples, and then treated again such that the treated cells flow into the well of the multi-well device.

The multi-well devices employed in the present disclosure (e.g., described in detail further below) may, in some embodiments, may constructed from a multi-well through-hole chip and PCR compatible film. A multi-well through-hole chip is, for example, the same as the multi-well devices described herein and known in the art (e.g., nano or micro wells, with hundreds or thousands of wells), except the openings for the "wells" extend through the substrate, forming holes instead of wells. A multi-well device may be formed from a multi-well through-hole chip by covering at least some, or all, for the holes on one side of the multi-well through-hole chip with PCR compatible film (e.g., Temp-Plate® PCR sealing film; VWR PCR sealing film; LABNET heat sealing film; BRANDTECH SCIENTIFIC Sealing film; AXYGEN SCIENTIFIC PCR-SP Sealing Films; etc.).

In particular embodiments, the multi-well device provided herein (e.g., including those made of PCR compatible film described above) are attached to the size exclusion polymer films described herein to form a device with size exclusion and multi-well device properties. In certain embodiments, the size exclusion polymer film is attached to the top of a multi-well device with double sized PCR compatible adhesive (e.g., 3M 9965 adhesive tape). In certain embodiments, once single cells are captured by the film and transferred to the wells of the multi-well device, lysis buffer is added to the wells (e.g., to start a whole-genome amplification or whole transcriptome amplification assay protocol).

In certain embodiments, a multi-well through-hole chip is provided which has a plurality of through-holes, where each of the through holes has a cell-sized opening on one side of the chip (e.g., 2-10 μm in diameter, or larger, depending on the size of the cells to be captured) and a larger reaction sized opening on the other side (e.g., 100-800 μm in diameter, or 400-500 μm in diameter). In some embodiments, chip has a thickness of at least 0.5 mm (e.g., at least 0.5 . . . 1.0 . . . 1.5 . . . 2.0 mm, or more). In particular embodiments, the chip is composed (e.g., mostly or entirely) out of silicon, quartz, glass, or a combination of such materials). In particular embodiments, two materials are bonded together (e.g., glass and silicon) to form the chip with the through-holes. In an exemplary embodiments a glass wafer (e.g., 500 um thick) (e.g., FORTRAN glass wafer) is bonded to a silicon wafer (e.g., 25 um thick) to form a bonded chip (e.g., that is about 525 um thick). Then, mask is aligned and patterned on the silicon side, and cell-sized holes (e.g., 4 um) are etched into the silicon down to the underlying glass layer. Then, a second mask is aligned on the glass side and larger reaction sized holes are etched in the glass, creating the multi-well through hole chip, where the holes are different sizes at each end.

The multi-well through-hole chips described herein, with different sized openings on each side, are first be used to capture single cells in the cell-sized openings. The cell-sized openings are sealed by applying a PCR compatible film to the chip, thus creating a multi-well device, where single cells are captured at the bottom of the formed wells. The multi-well device is then used as described herein by, for example, adding lysis and amplification reagents through the reaction sized holes.

In certain embodiments, provided herein are capture-chips that contain a plurality of cell-sized spots or dimples (e.g., mini-wells) that each allow a single cell to be captured from a cell mixture. In some embodiments, the cell-sized dimples are etched into a substrate (e.g., composed of glass, silicon, quartz, or combination thereof). In particular embodiments, plasma etching is employed. An exemplary protocol is as follows. A substrate mask is placed on a substrate which has been coated with photoresist (e.g., Shipley 1818) and exposed to create the dimples. The photomask is manufactured by a direct laser writer such as Heidelberg Instruments. Once the substrate has the etched spots/dimples, a cell suspension is flowed over the etched chip (e.g., in a flow cell), and single cells are captured in the spots/dimples. The excess cells are then washed off, and the capture-chip is aligned with a multi-well device as described herein, such that the dimples on the capture chip align with the wells of the multi-well device. The wells of the multi-well device may be pre-filled with reagents, such as lysis and/or amplification reagents. The mated devices are then centrifuged (or otherwise agitated) such that the reagents in the multi-well device travel towards and contact the cell in the dimple (e.g., lysing or otherwise releasing the cell from any attachment to the dimple). The mated device is then centrifuged (or otherwise agitated in the opposite direction) such that the cell (or lysed cell contents) travel the opposite way, into the wells of the multi-well device. The capture chip is then removed, and the multi-well device, with wells each containing a single cell (or single cell contents) is treated in a biological reaction (e.g., in a PCR or similar reaction).

Another exemplary embodiment of the systems and methods of the present invention is as follows. A system of the present invention may be composed of a hydrophobic or super hydrophobic (e.g., Fluorosilane coated) polymer film stretched across an open frame and drilled by a laser or similar device. The diameter of the channels created and the thickness of the film is selected such that one single cell can be contained in each channel. The pitch of the channels or pattern will be matched to the pattern of holes on a multi-well device, such as WAFERGEN's 5184 SmartChip, that can be used to perform a single cell assay. This polymer film is backed by a rigid porous foam that is selected to have pores that may be hydrophilic or hydrophobic but will allow only the cell suspension buffer to pass through but block the cells itself. This sandwich is assembled into an assembly that enables the user to introduce a cell suspension while a source of negative pressure is applied behind the foam. This entire assembly may be positioned on an agitator or gyrator to move the cell suspension on top of the polymer film to enable single cells to be captured by the negative pressure inside each of the channels in the polymer film. The single cells cannot pass through the foam only the suspension liquid will pass through. The negative pressure may be monitored with a high precision gauge to indicate when all the channels in the polymer film have been occluded by cells. Because the polymer film is hydrophobic or coated with a superhydrophobic coating such as Fluorosilane, the suspended cells will generally not attach itself singly or in clumps to the surface. Once it is deemed that the cells have been captured, the excess cell suspension may be flushed out with cell free buffer such as PBS to remove the excess cells while some level of negative pressure is applied to keep the captured cells from flowing away. After the removal of excess cells and cell suspension buffer, there will be single cells captured on the film and then a multi-well device (e.g., SmartChip) may be placed face down on the film and the assembly placed in a centrifuge fixture to transfer the single cells individually into the multi-well device wells. The multi-device wells may have preloaded cell buffer to keep the cells alive or could be preloaded with cell lysis buffer. The multi-well device may can now be filled with various assay reagents by a multi-sample nano-dispenser for gene expression or sequencing.

Another exemplary embodiment of the systems and methods of the present invention is as follows. In particular, another method of isolation and capture of cells may be accomplished on the surface of a polymer that has channels drilled on pitch as a multi-well device (e.g., Smartchip) but sized such that a single cells can be captured but not go through. The capture of the cells may be accomplished by negative pressure which is being imparted behind the porous foam. This method will not require a polymer film of the same thickness (as above) as the cells will be captured on the surface instead of inside the channels of the film. This method of surface capture will also enable efficient washing away of the excess cells while the captured cell will be held in place on top of the channel by negative pressure.

Another method of the transfer of the captured cells may be accomplished by pushing off the captured cell from the polymer surface or the channel in the film by reversing the negative to positive pressure and using the cell suspension buffer liquid to wash the cell from the surface or the channel into the wells of a multi-well device (e.g., SmartChip).

Another alternative exemplary embodiment is described as follows. An alternate method of isolation may be fabricated using a super hydrophobic surface (e.g., Fluorosilane) that will prevent cells from sticking. The surface of this super hydrophobic may have small islands of polydopamine or other hydrophilic material that would allow a cell to adhere to it. Thus a super hydrophobic surface with islands about the size of the target cells could be part of a flow cell where the cells of interest suspended in a suspension buffer would flow over this surface and single cells would be captured on the "islands" of polydopamine or other hydrophilic material. The pattern and size of islands (or "spots") could be such that after the excess cells have been washed off a multi-well device such as a Smartchip could be placed face down using a simple pin alignment scheme such that each island of captured single cell will be centered in one of the wells of the multi-well device (e.g., SMARTCHIP). Then using a centrifuge, each captured single cell could be transferred into the wells of the multi-well device (e.g., SMARTCHIP).

The size of the single cells one wishes to isolate will dictate the size of the channels or hydrophilic spots on the polymer that are employed. The channels in the polymer need to be at least slightly bigger than the desired cells in order to capture the cells in the channel. If one wishes to capture the cells on the surface of the polymer with channels, the diameter of the channels should be at least slightly smaller than the target cells. In regard to the hydrophilic spots, these spots should be about the size of the target cell. The size of most human cells fall within a size range of 2-120 microns. Platelets are ~2 microns, red cells ~3 microns×~8 microns, neutrophils ~8-10 microns, lymphocytes ~6-12 microns in size, exocrine cells ~10 microns, fibroblasts 10-15 microns, osteocytes ~10-20 microns including processes, chondrocytes and liver cells ~20 microns, goblet and ciliated cells ~50 microns long and 5-10 microns wide, macrophages at ~20-80 microns, hematopoietic stem cells ~30-40 microns, and adipocytes filled with stored lipid are typically 70-120 microns in diameter (but may be up to five times larger in very obese people). Neurons vary enormously in size and shape, their bodies ranging from 4-120 microns in diameter with axonal processes varying between ~0.1-20 microns in diameter and ranging in length from a few microns up to ~1 meter; muscle cells (~30% of all tissue cells) also vary from 10-100 microns in diameter and may run up to ~50 cm in length.

The present invention is not limited by the type of multi-well devices (e.g., plates or chips) employed or that the channels and spots on the polymer are designed to mate with. In general, such devices have a plurality of wells that contain, or are dimensioned to contain, liquid (e.g., liquid that is trapped in the wells such that gravity alone cannot make the liquid flow out of the wells). One exemplary chip is WAFERGEN's 5184-well SMARTCHIP. Other exemplary chips are provided in U.S. Pat. Nos. 8,252,581; 7,833,709; and 7,547,556, all of which are herein incorporated by reference in their entireties including, for example, for the teaching of chips, wells, thermocycling conditions, and associated reagents used therein). Other exemplary chips include the OPENARRAY plates used in the QUANTSTUDIO real-time PCR system (Applied Biosystems). Another exemplary multi-well device is a 96-well or 384-well plate.

The overall size of the multi-well devices may vary and it can range, for example, from a few microns to a few centimeters in thickness, and from a few millimeters to 50 centimeters in width or length. Typically, the size of the entire device ranges from about 10 mm to about 200 mm in width and/or length, and about 1 mm to about 10 mm in thickness. In some embodiments, the chip is about 40 mm in width by 40 mm in length by 3 mm in thickness.

The total number of wells (e.g., nanowells) on the multi-well device may vary depending on the particular application in which the subject chips are to be employed. The density of the wells on the chip surface may vary depending on the particular application. The density of wells, and the size and volume of wells, may vary depending on the desired application and such factors as, for example, the species of the organism for which the methods of this invention are to be employed.

The present invention is not limited by the number of wells in the multi-well device. A large number of wells may be incorporated into a device. In various embodiments, the total number of wells on the device is from about 100 to about 200,000, or from about 5000 to about 10,000. In other embodiments the device comprises smaller chips, each of which comprises about 5,000 to about 20,000 wells. For example, a square chip may comprise 125 by 125 nanowells, with a diameter of 0.1 mm.

The wells (e.g., nanowells) in the multi-well devices may be fabricated in any convenient size, shape or volume. The well may be about 100 μm to about 1 mm in length, about 100 μm to about 1 mm in width, and about 100 μm to about 1 mm in depth. In various embodiments, each nanowell has an aspect ratio (ratio of depth to width) of from about 1 to about 4. In one embodiment, each nanowell has an aspect ratio of about 2. The transverse sectional area may be circular, elliptical, oval, conical, rectangular, triangular, polyhedral, or in any other shape. The transverse area at any given depth of the well may also vary in size and shape.

In certain embodiments, the wells have a volume of from about 0.1 nl to about 1 μl. The nanowell typically has a volume of less than 1 μl, preferably less than 500 nl. The volume may be less than 200 nl, or less than 100 nl. In an embodiment, the volume of the nanowell is about 100 nl. Where desired, the nanowell can be fabricated to increase the surface area to volume ratio, thereby facilitating heat transfer through the unit, which can reduce the ramp time of a thermal cycle. The cavity of each well (e.g., nanowell) may take a variety of configurations. For instance, the cavity within a well may be divided by linear or curved walls to form separate but adjacent compartments, or by circular walls to form inner and outer annular compartments.

A well of high inner surface to volume ratio may be coated with materials to reduce the possibility that the reactants contained therein may interact with the inner surfaces of the well if this is desired. Coating is particularly useful if the reagents are prone to interact or adhere to the inner surfaces undesirably. Depending on the properties of the reactants, hydrophobic or hydrophilic coatings may be selected. A variety of appropriate coating materials are available in the art. Some of the materials may covalently adhere to the surface, others may attach to the surface via non-covalent interactions. Non-limiting examples of coating materials include silanization reagent such as dimethychlorosilane, dimethydichlorosilane, hexamethyldisilazane or trimethylchlorosilane, polymaleimide, and siliconizing reagents such as silicon oxide, AQUASIL, and SURFASIL. Additional suitable coating materials are blocking agents such as amino acids, or polymers including but not limited to polyvinylpyrrolidone, polyadenylic acid and polymaleimide. Certain coating materials can be cross-linked to the surface via heating, radiation, and by chemical reactions. Those skilled in the art will know of other suitable means for coating a nanowell of a multi-well device, or will be able to ascertain such, without undue experimentation.

An exemplary multi-well device (e.g., chip) may have a thickness of about 0.625 mm, with a well have having dimensions of about 0.25 mm (250 um) in length and width. The nanowell depth can be about 0.525 mm (525 um), leaving about 0.1 mm of the chip beneath a given well. A nanowell opening can include any shape, such as round, square, rectangle or any other desired geometric shape. By way of example, a nanowell can include a diameter or width of between about 100 μm and about 1 mm, a pitch or length of between about 150 μm and about 1 mm and a depth of between about 10 μm to about 1 mm. The cavity of each well make take a variety of configurations. For instance, the cavity within a nanowell may be divided by linear or curved walls to form separate but adjacent compartments.

The wells (e.g., nanowells) of the multi-well device may be formed using, for example, commonly known photolithography techniques. The nanowells may be formed, for example, using a wet KOH etching technique, an anisotropic dry etching technique, mechanical drilling, injection molding and or thermo forming (e.g., hot embossing).

Reagents contained within the liquid in the multi-well device depend on the reaction that is to be run with the single cell that is deposited into each well. In an embodiment, the wells contain a reagent for conducting the nucleic acid amplification reaction. Reagents can be reagents for immunoassays, nucleic acid detection assays including but not limited to nucleic acid amplification. Reagents can be in a dry state or a liquid state in a unit of the chip. In an embodiment, the wells contain at least one of the following reagents: a probe, a polymerase, and dNTPs. In another embodiment, the wells contain a solution comprising a probe, a primer and a polymerase. In various embodiments, each well comprises (1) a primer for a polynucleotide target within said standard genome, and (2) a probe associated with said primer which emits a concentration dependent signal if the primer binds with said target. In various embodiments, each well comprises a primer for a polynucleotide target within a genome, and a probe associated with the primer which emits a concentration dependent signal if the primer binds with the target. In another embodiment, at least one well of the chip contains a solution that comprises a forward PCR primer, a reverse PCR primer, and at least one FAM labeled MGB quenched PCR probe. In an embodiment, primer pairs are dispensed into a well and then dried, such as by freezing. The user can then selectively dispense, such as nano-dispense, the sample, probe and/or polymerase.

In other embodiments of the invention, the wells may contain any of the above solutions in a dried form. In this embodiment, this dried form may be coated to the wells or be directed to the bottom of the well. The user can add a mixture of water and the captured cells to each of the wells before analysis. In this embodiment, the chip comprising the dried down reaction mixture may be sealed with a liner, stored or shipped to another location.

The multi-well devices, with a single cell in each well, may be used for genotyping, gene expression, or other DNA assays preformed by PCR. Assays performed in the plate are not limited to DNA assays such as TAQMAN, TAQMAN Gold, SYBR gold, and SYBR green but also include other assays such as receptor binding, enzyme, and other high throughput screening assays. In some embodiments, a ROX labeled probe is used as an internal standard.

Another exemplary embodiment of the present disclosure is presented in the paragraphs below, describing the initial construction and use of a housing assembly to capture single cells using a polymer capture film, as well as assembly of a multi-well chip for processing each captured single cell (e.g., for sequencing the mRNA of each captured single cell). This discussion is generally with reference to FIG. 2-9, which are provided as exemplary embodiments only.

A multi-well chip can be generated by combining a through-hole chip and an adhesive sealing film to form the bottom of the wells in the multi-well chip. A through-hole chip may be generated by drilling a plurality of holes in a planar, relatively hard and relatively thin material such as metal (e.g., aluminum), silicon, ceramic, and related materials. The thickness of the material depends on the desired depth of each well, and may be, in some embodiments, between 1.0 and 9.0 mm (e.g., 1.0 . . . 2.7 . . . 3.4 . . . 5.0 . . . 7 mm). Holes may be drilled through this material using any number of suitable techniques, including mechanical drilling on a programmable high speed precision drilling machine (e.g., the Kern HSPC 25 drilling machine made by Kern Precision, Inc.). For example, a metal substrate (e.g., aluminum) may be mechanically drilled on a programmable high speed precision drilling machine. Typically a 3D CAD design file such as STEP AP214 is converted to the appropriate machine commands which then executes the drill pattern and depth using the correct diameter drill. The diameter of the holes drilled may vary depending the desired diameter of the final wells. In some embodiments, the diameter of each hole drilled in the material is between 0.20 and 2.5 mm (e.g., 0.2 . . . 0.45 . . . 1.5 . . . 2.5 mm). The number of holes depends on the number of desired wells. In certain embodiments, the number of holes drilled is between 2 and 30,000 (e.g., 2 . . . 15 . . . 50 . . . 96 . . . 386 . . . 1000 . . . 3000 . . . 5184 . . . 15,000 . . . 30,000 holes). In particular embodiments, a grid of 72×72 is programmed into the drilling machine to generate a through-hole chip with 5184 holes. In certain embodiments, the through-hole is then treated such that each channel (that will become a well) is coated with a hydrophobic coating (e.g., an example of such a coating is a parylene conformal coating), to make the final wells bio-compatible. Finally, a sealing film is added to one side of the through-hole chip to form the bottom of each well (e.g., using a low tack sealing film).

A housing assembly containing the polymer capture film and related components for isolating single cells (for use with a multi-well chip) can be created by the exemplary embodiments described below.

Figure 1B:
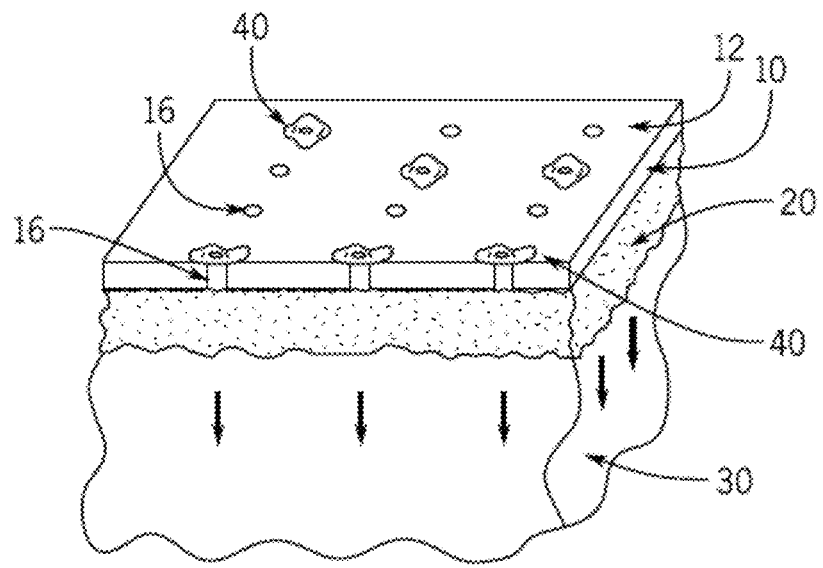
FIG. 1B shows an alternative exemplary embodiment and generally shows the same components as FIG. 1A, except that channels (14) in the polymer film (10) are smaller than the cells (40) such that the cells are captured on the top surface (12) of the polymer film (10).

Three of the components inside the housing assembly (e.g., housing assembly shown in FIG. 2) are generated with holes that align with the wells of the multi-well chip. These three components include the double sided adhesive, polymer capture film, and the film support plate (if a film support plate is used instead of a porous layer as shown in FIG. 1). The double sided adhesive (e.g., 3M 9965 pressure sensitive adhesive), which may have two release layers and carrier in the middle (e.g., all made of polyester), is drilled (e.g., laser drilled) on the same pitch as the through-hole chip. The holes that are drilled are generally smaller (e.g., 5-50% smaller) than the holes drilled in the corresponding through-hole chip. In certain embodiments, the holes drilled are between 0.10 mm and 4.0 mm (e.g., 0.1 . . . 0.350 . . . 2.0 . . . and 4.0 mm). The drilling of the double sided adhesive may be accomplished by using an Excimer laser (e.g., manufactured by Potomac Photonics) that has a programmable X-Y table. Similar to the precision drill discussed above, a 3D CAD file is loaded to drill the holes on the same pitch as the through hole chip.

The holes in the polymer capture film may be made in the same type of manner as for the double sided adhesive using a laser drill for example, using the same pitch as for the through hole pitch. The diameter of the holes created as such that single cells will be captured near the top, or inside, the holes (channels). Such holes depend on the type of cell that is being isolated (e.g., single cell per channel). An exemplary size range is from 2 to 35 microns (e.g., 2 . . . 4 . . . 25 . . . or 35 microns). The film may be any type of suitable material, including a polymer that is inert and hydrophobic (e.g., polyimide film, such as KAPTON film from DuPont, polyester, polyethylene, polyurethane, TEFLON and/or PTFE; see also Vladkova, T. G. (2010) "Surface engineered polymeric biomaterials with improved biocontact properties." Int. J. Polym. Sci., 2010, 1-22, herein incorporated by reference in its entirety, particularly for the polymers discussed therein). The thickness of the film, in certain embodiments, is between 10 um and 50 um (e.g., 10 . . . 25 . . . 35 . . . and 50 um). In particular embodiments, the aspect ratio (diameter of hole vs. thickness of polymer) is about 5:1, 6:1, or 7:1.

The holes in the film support component, in certain embodiments, using the same type of methods, materials, and devices as the through-hole chip (see above), using the same pitch as for the through-hole chip. In certain embodiments, the diameter of the holes in the film support component is the same or similar to that of the through-hole chip (see above). For example, the film support component may have holes with diameters of between 0.20 and 2.5 mm (e.g., 0.2 . . . 0.45 . . . 1.5 . . . 2.5 mm). The film support component may have a thickness similar to the that of the though-hole chip, or may be thinner (e.g., about 0.9-1.1 mm thick aluminum or other metal or material).

A slot array component (e.g., part 180 in FIGS. 2, 5A, and 5B) may be fabricated with a plurality of slots (e.g., equal to the number of rows of channels/holes in the polymer capture film), using the same pitch as the holes in the polymer capture film. The slot array component is, in certain embodiments, sized based on the size of the polymer capture film, such that the slots can deliver cell-containing liquid to the top of the holes/channels in the polymer film. An exemplary size is 400 um wide×200 um deep. The slot array component can be manufactured by injection mold fabrication and vapor polished. In certain embodiments, the slot array is made of a thermoplastic polymer (e.g., polycarbonate) or other type of plastic.

Figure 2:
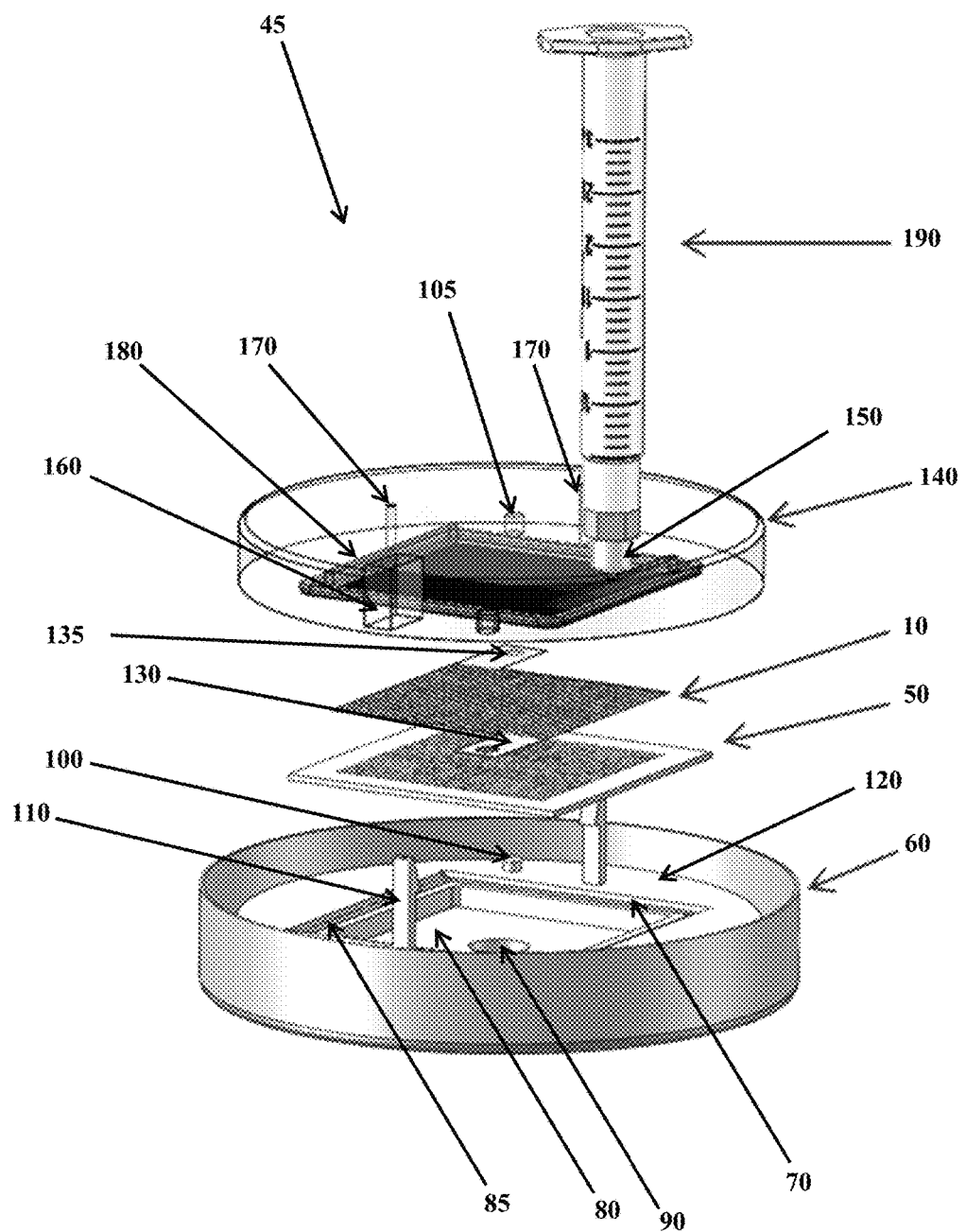
FIG. 2 shows an exemplary housing assembly (45) with an exemplary attached sample delivery component (190). The housing assembly (45) has a housing base (60) that has an interior top surface (120) which has two guide pins (100) therein. The housing base (60) also has a liquid reservoir (80), a film support recess (70) and corresponding gasket (85), as well as a vacuum connection port (90) in the bottom of the reservoir (80). The housing base (60) also has a pair of connection rods (110) to connect the housing base (60) to the housing top (140). Housing top (140) has an inlet port (150) and an outlet port (160). The inlet port (150) connects to a sample delivery component (190), shown as a syringe in this figure. The housing top (140) has a slot array (180), and a pair of connection rod receivers (170), for connection to the connection rods (110). The housing top (140) also has two guide pin receivers (105). The exemplary housing assembly (45) also has a polymer capture film (10) that sits on a film support component (50). The polymer capture film (10) has a pair of film guide components (130), that each have a film guide pin receiver (135) for receiving the guide pins (100). The film support component (50) is configured to sit in the film support recess (70) such that the guide pins (100) insert into the film guide pin receivers (135), thereby aligning the plurality of individual cell capturing channels in the polymer film to align with the plurality of holes in the film support component (50).

An exemplary housing assembly may be assembled with some or all of the components shown in FIG. 2, and used to capture single cells on the polymer capture film. FIG. 2 shows an exemplary housing assembly (45) with an exemplary attached sample delivery component (190). Other shapes for the housing assembly may be employed besides the circular shape shown in FIG. 2, and the square shape shown in FIG. 3. The housing assembly may be composed of any suitable material, including plastic. The sample delivery component (190) is shown as a syringe in FIG. 2, but may be other devices that can mate with the inlet port (150), such as a pipette or similar devices. The housing assembly (45) has a housing base (60) that has an interior top surface (120) which has two guide pins (100) thereon. The housing base (60) also has a liquid reservoir (80), a film support recess (70) and corresponding gasket (85), as well as a vacuum connection port (90) in the bottom of the reservoir (80). The housing base (60) also has a pair of connection rods (110) to connect the housing base (60) to the housing top (140). Housing top (140) has an inlet port (150) and an outlet port (160). The inlet port (150) connects to a sample delivery component (190), shown as a syringe in this figure. The housing top (140) has a slot array (180), and a pair of connection rod receivers (170), for connection to the connection rods (110). The housing top (140) also has two guide pin receivers (105). The exemplary housing assembly (45) also has a polymer capture film (10) that sits on a film support component (50). The polymer capture film (10) has a pair of film guide components (130), that each have a film guide pin receiver (135) for receiving the guide pins (100). Such film guide components may be flaps or other protrusions from the polymer capture film that have a hole or other attachment component. The film support component (50) is configured to sit in the film support recess (70) such that the guide pins (100) insert into the film guide pin receivers (135), thereby aligning the plurality of individual cell capturing channels in the polymer film to align with the plurality of holes in the film support component (50). The polymer capture film is placed on top of the film support component such that the holes in the polymer capture film (e.g., 4 um) line up on center with the 400 um holes of the film support component. In other embodiments, a porous layer (part 20 in FIG. 1) is used instead of the filmy support component.

Figure 3A:
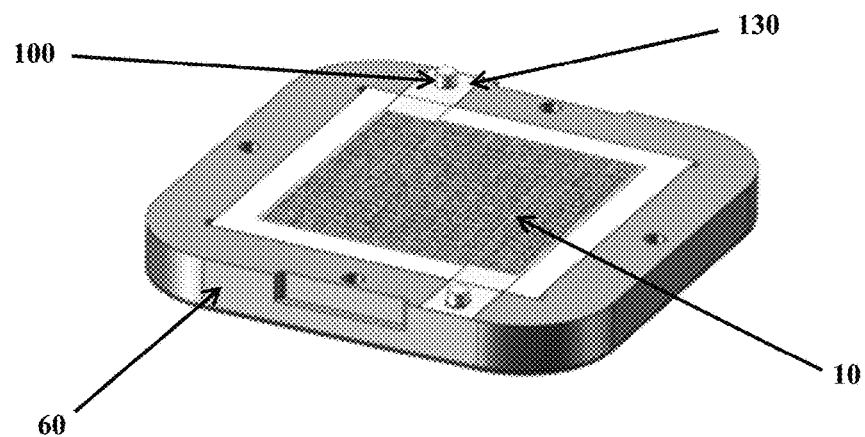
FIG. 3A shows an exemplary housing base (60) with two guide pins (100), polymer capture film (10), and film guide components (130).
Figure 3B:
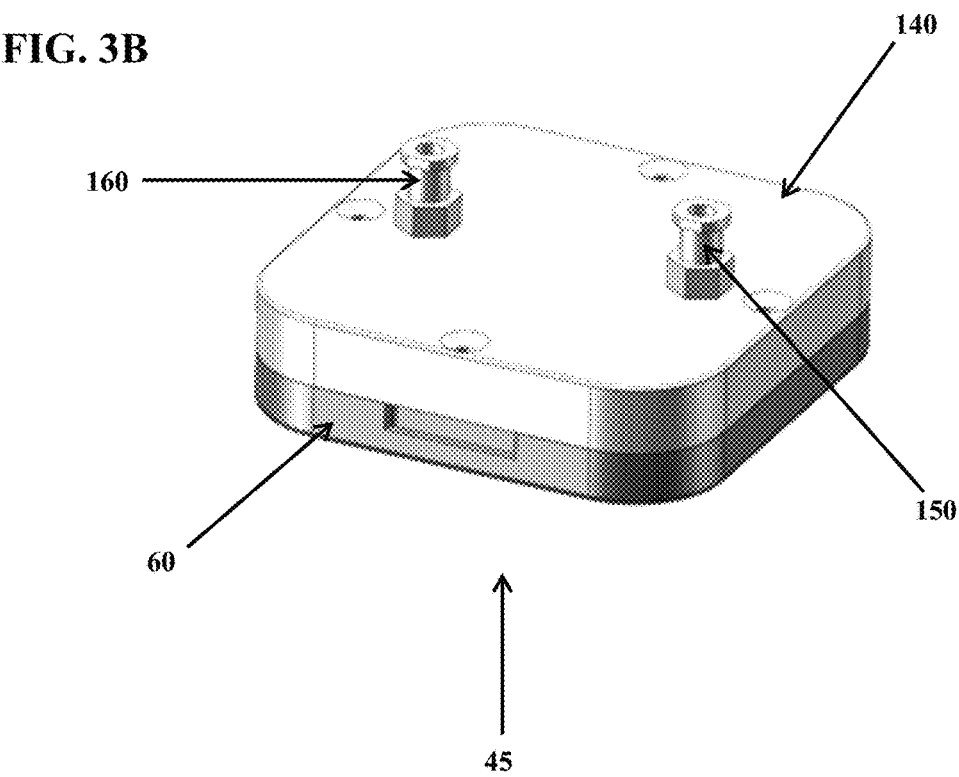
FIG. 3B shows an exemplary housing assembly (45) with a housing base (60) and housing top (140). The housing top (140) is shown with an inlet port (150) and an outlet port (160).

FIG. 3A shows an exemplary housing base (60) with two guide pins (100), polymer capture film (10), and film guide components (130). In certain embodiments, the guide pins (100) are rods, or cones, or other useful shape. FIG. 3B shows an exemplary housing assembly (45) with a housing base (60) and housing top (140). The housing top (140) is shown with an inlet port (150) and an outlet port (160). The inlet port (150) is shaped and sized to accommodate the chosen sample delivery component (190).

Figure 4:
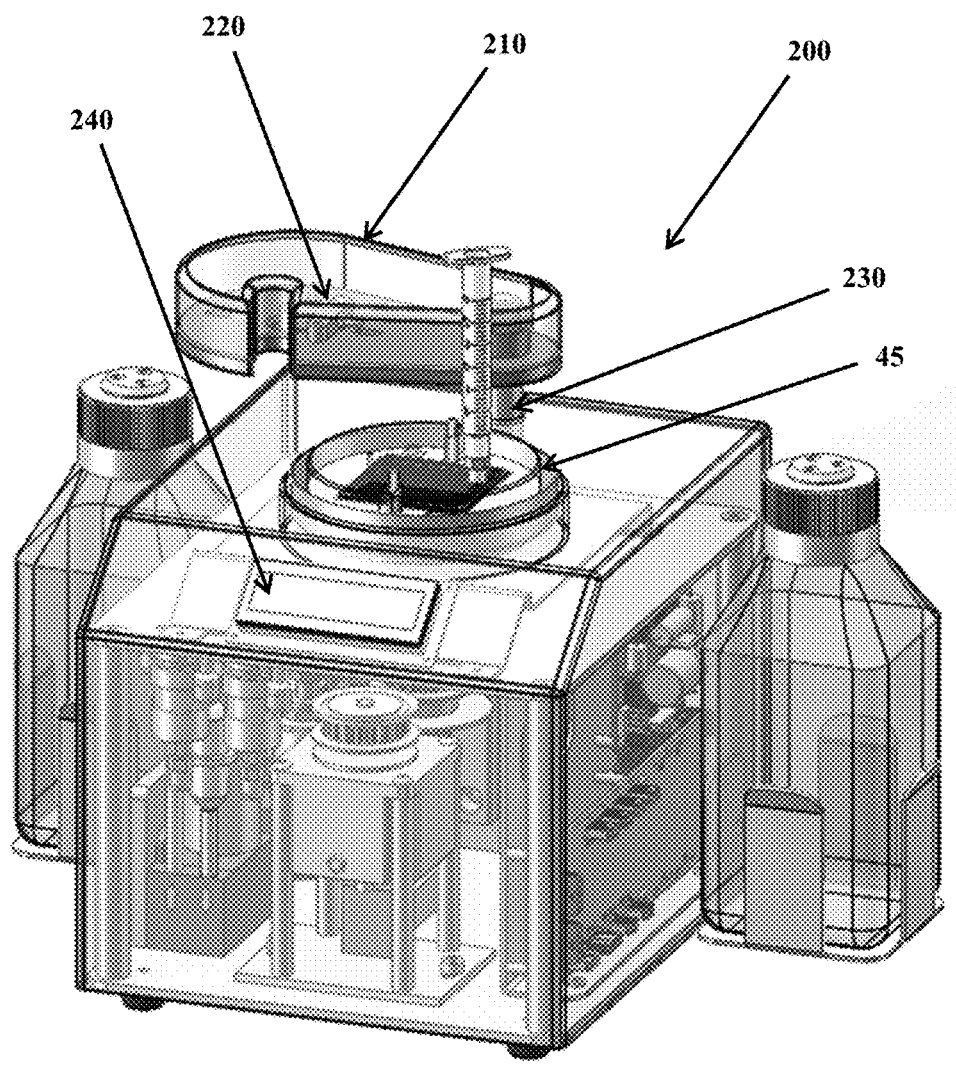
FIG. 4 shows an exemplary cell capture instrument (200) with a housing assembly (45) and a swing arm (210) that has a drain port (220) designed to engage with the outlet port (160). The cell capture instrument also has a user interface display (240).

FIG. 4 shows an exemplary cell capture instrument (200) with a housing assembly (45) and a swing arm (210) that has a drain port (220) designed to engage with the outlet port (160). The cell capture instrument also has a user interface display (240). In general, a user places the housing assembly into the cell capture instrument and starts a software program in the instrument (e.g., a software program operably linked to a processor and the various components of the cell capture instrument which controls the timing and functions of the various components).

Figure 5A:
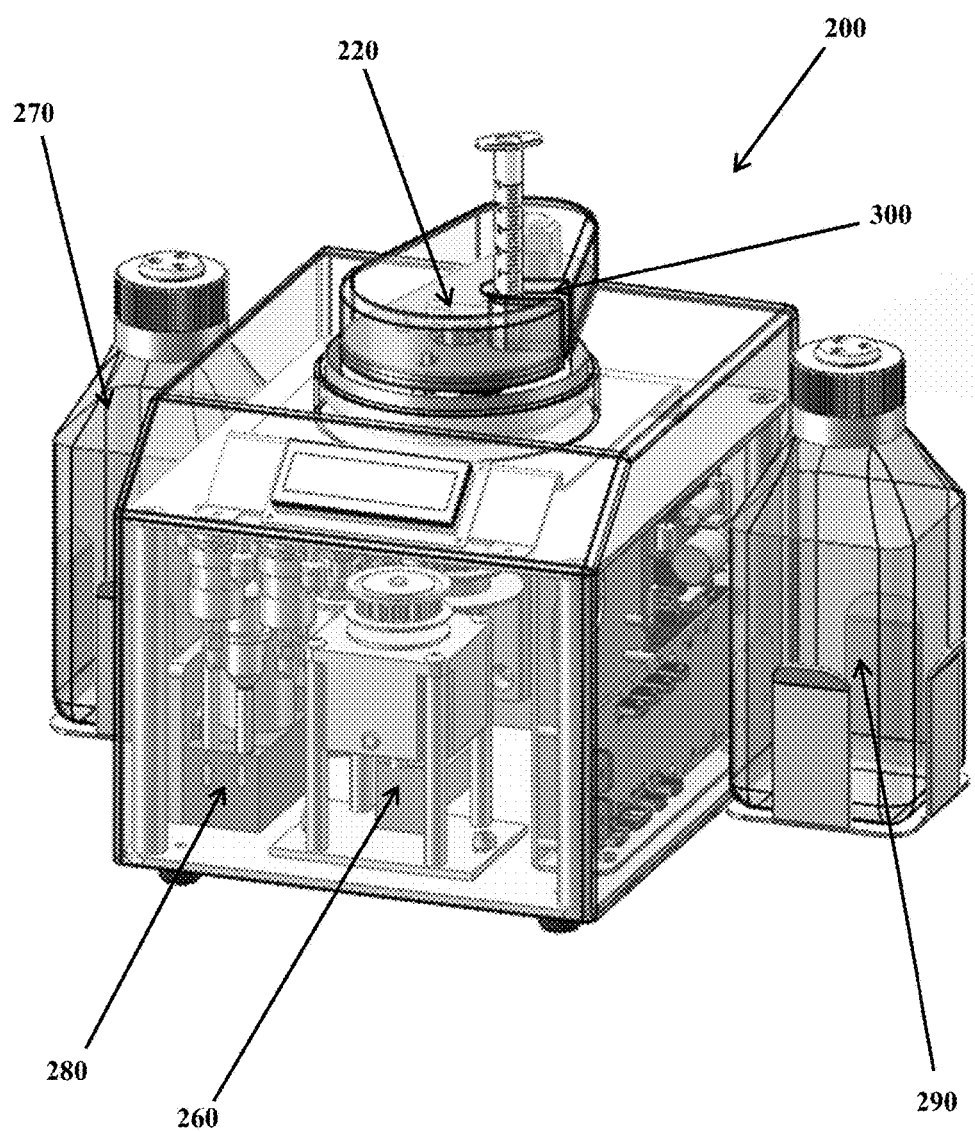
FIG. 5A shows an exemplary cell capture instrument (200) with a swing arm (210) having a swing arm sample delivery slot and a drain port (220). The exemplary cell capture instrument (200) also has a vacuum pump (280), first waste collection container (270), a diaphragm pump (260), and a second waste collection container (290).
Figure 5B:
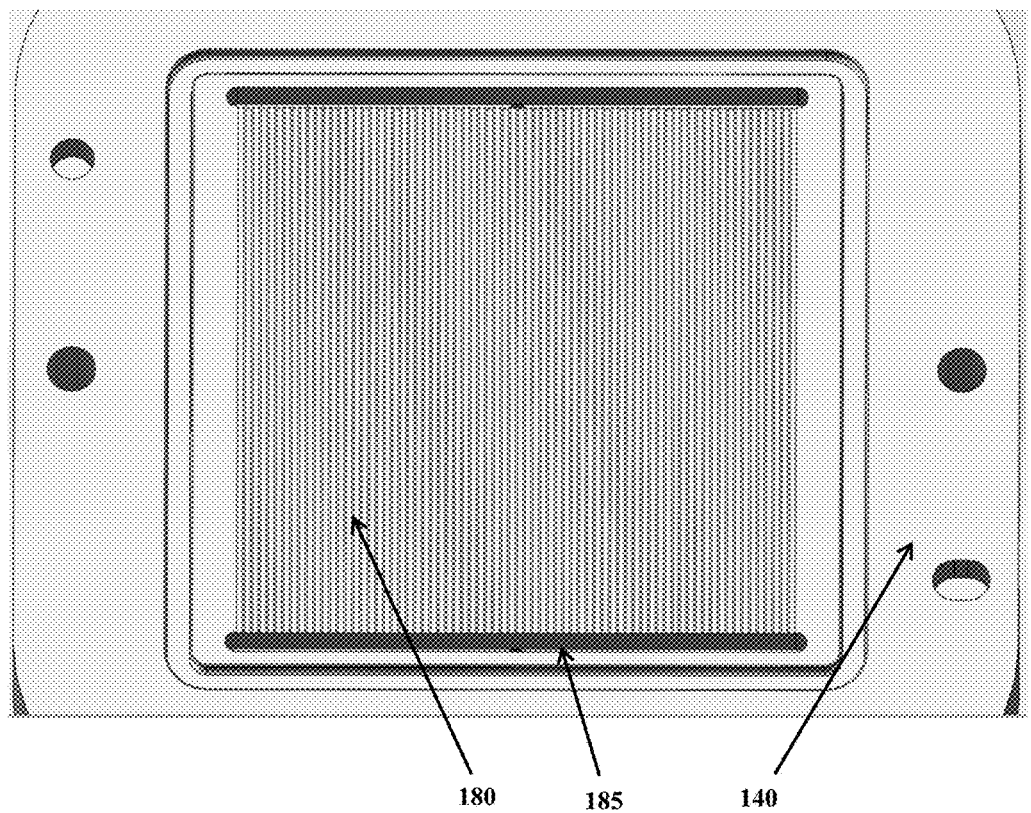
FIG. 5B shows a slot array (180), with a plurality of slots, which terminate in a pair of slot array headers (185).
Figure 5C:
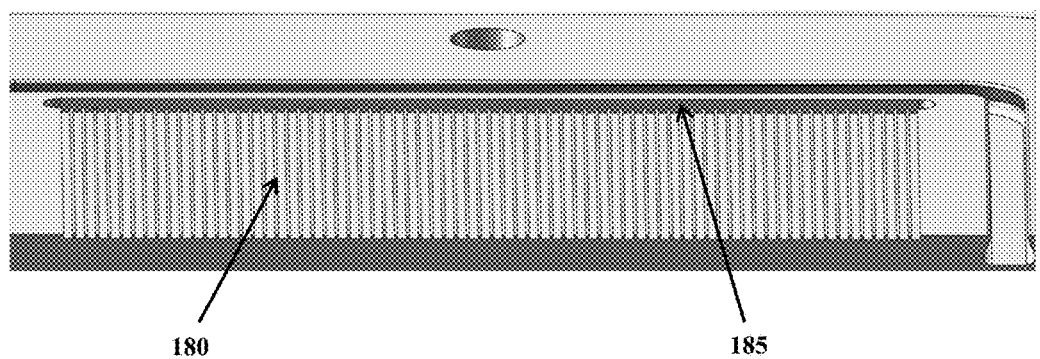
FIG. 5C shows a close up perspective view of a slot array (180) with a plurality of headers (72 shown in this figure) that terminate in a slot array header (185).

FIG. 5A shows an exemplary cell capture instrument (200) with a swing arm (210) having a swing arm sample delivery slot and a drain port (220). The exemplary cell capture instrument (200) also has a vacuum pump (280) (operably linked to vacuum connection port 90), first waste collection container (270) (e.g., for receiving liquid from connection port 90), a diaphragm pump (260) (e.g., for moving liquid containing cells around in the housing assembly), and a second waste collection container (290) (e.g., serving as a vacuum trap for liquid). FIG. 5B shows a slot array (180), with a plurality of slots, which terminate in a pair of slot array headers (185). FIG. 5C shows a close up perspective view of a slot array (180) with a plurality of headers (72 slots shown in this figure) that terminate in a slot array header (185). The slot array header is operably connected to an inlet port (150) (e.g., a luer connection). In certain embodiments, each slot in the slot array is designed to be directly over the array of holes in the polymer capture film. In certain embodiments, each slot terminates at both ends into header that is used to feed the slots or drain them. In general, the purpose of the slots are to flow the cell suspension liquid directly over each row of holes that are in the polymer capture film, which helps ensure that the cells are not generally flowing around in a random manner. Therefore, in certain embodiments, due to this type of flow control, the cell suspension can be moved back and forth by alternating the pressure between the inlet and the outlet ports (e.g., to increase the capture efficiency).

Returning to FIG. 5A, a diaphragm vacuum pump (260) with a regulator is connected via liquid trap to the outlet port (160). When the program is started, the swing arm moves over the housing assembly and clamps it down. A 10 ml plastic syringe with a buffer (e.g., 3 ml of 1×PBS) is connected to the inlet port. Vacuum pump (280) is activated to provide negative pressure (e.g., 12" Hg negative pressure) to the bottom of housing assembly to move the liquid down from the syringe and pre-wet the capture holes in the polymer capture film. The vacuum then stops, and another 10 ml syringe filled with a cell suspension (e.g., $2 \times 10^5$ cells) is connected to the inlet port. The diaphragm pump (260), connected to the outlet port (160), is activated while the cells suspension is slowly injected into the inlet port (150). Cells are pulled through the housing assembly (guided by the slow array (180)), using the diaphragm pump at the outlet port side (e.g., using a vacuum set to 4" Hg). The diaphragm pump stops, while the vacuum pump (280) maintains a vacuum (e.g., at 4" hg) for capture of the cells by the polymer capture film. At this point, at least some of the individual channels/holes in the polymer capture film have a single cell in or captured atop the channel/hole (e.g., see FIG. 1). After about 3-10 minutes (e.g., about 5 minutes), the syringe is removed, and then a syringe with buffer (e.g., 10 ml of 1×PBS) is introduced into the inlet port and pulled through the assembly for an initial rinse.

Figure 6A:
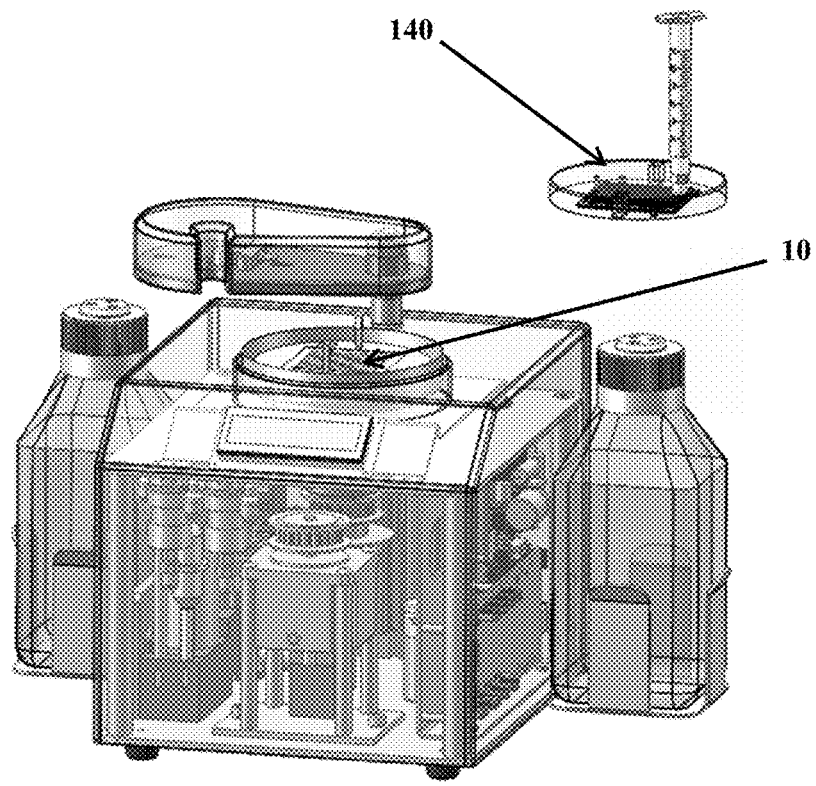
FIG. 6A shows an exemplary call capture instrument (200) with the housing top (140) removed, revealing the polymer capture film (10).
Figure 6B:
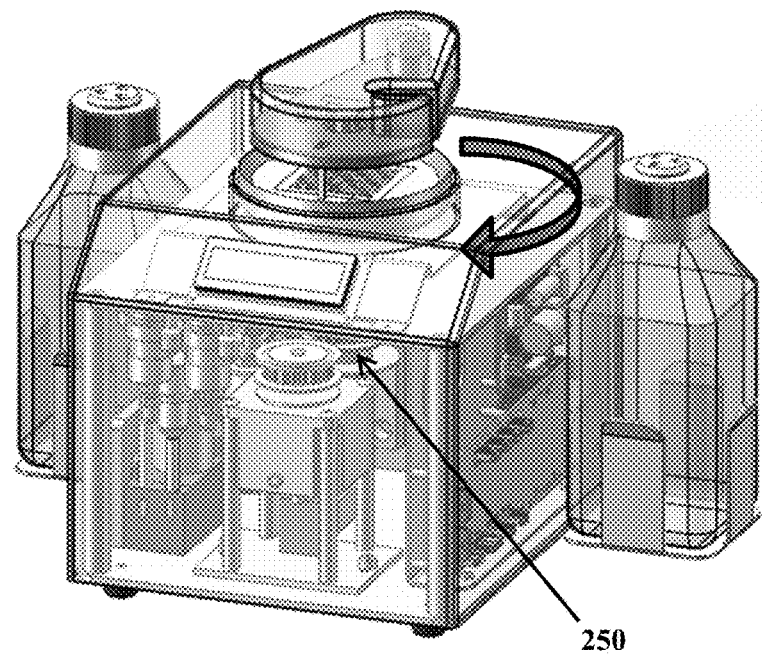
FIG. 6B shows that centrifuge motor (250) below the housing base (60) containing the polymer capture film (10) on the film support component (50).

FIG. 6A shows an exemplary call capture instrument (200) with the housing top (140) removed, revealing the polymer capture film (10). FIG. 6B shows that centrifuge motor (250) below the housing base (60) containing the polymer capture film (10) on the film support component (50). Next, with the capture cycle complete, with the vacuum for the polymer capture film still on (e.g., at 4" hg), the swing arm moves up and over to permit access to the housing assembly. The housing top (140) is then removed. At this point, the housing base (with polymer capture film) is centrifuged using the centrifuge motor (250) shown in FIG. 6 to remove any excess wash buffer. Buffer may be sprayed on the film to complete rinse of excess cells. Centrifuging also allows the creation of a dry surface on the polymer capture film to have a dry surface for bonding the multi-well chip to the polymer capture film.

Figure 7A:
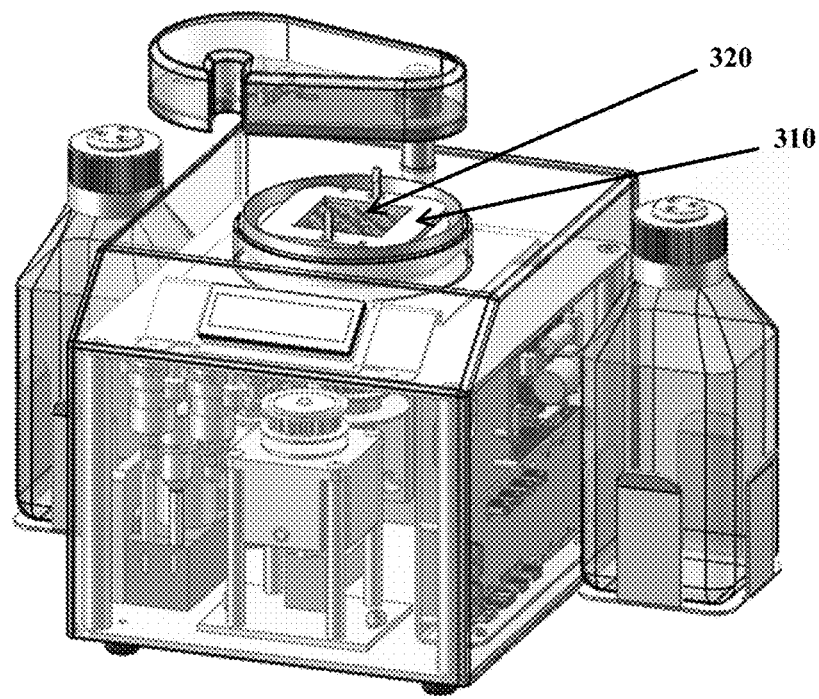
FIG. 7A shows a chip alignment component (310) placed down on the guide pins (100). A multi-well chip (320) is shown placed inside the chip alignment component (310), on top of the polymer capture film (10).
Figure 7B:
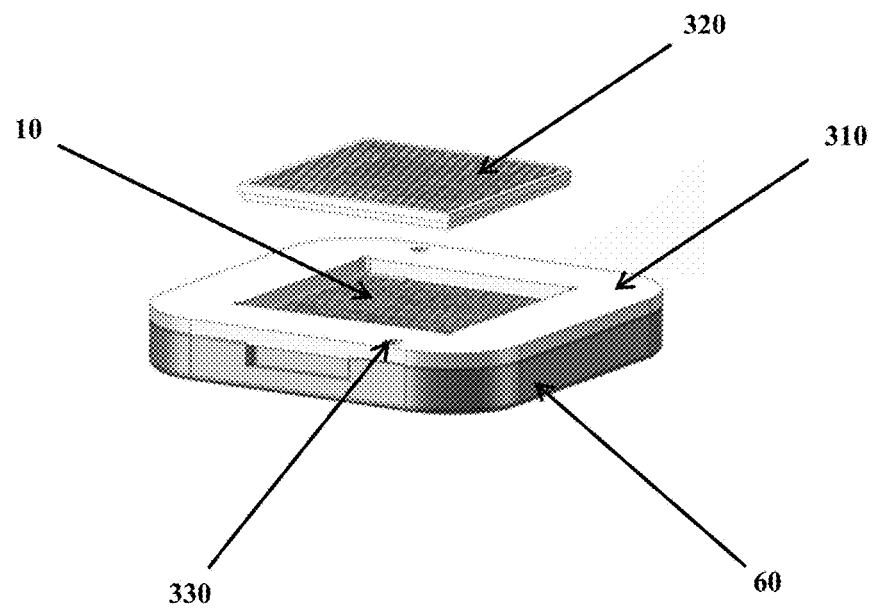
FIG. 7B shows a chip alignment component (310) on top of the housing base (60), as well as a multi-well chip (320) above the polymer capture film (10).
Figure 8:
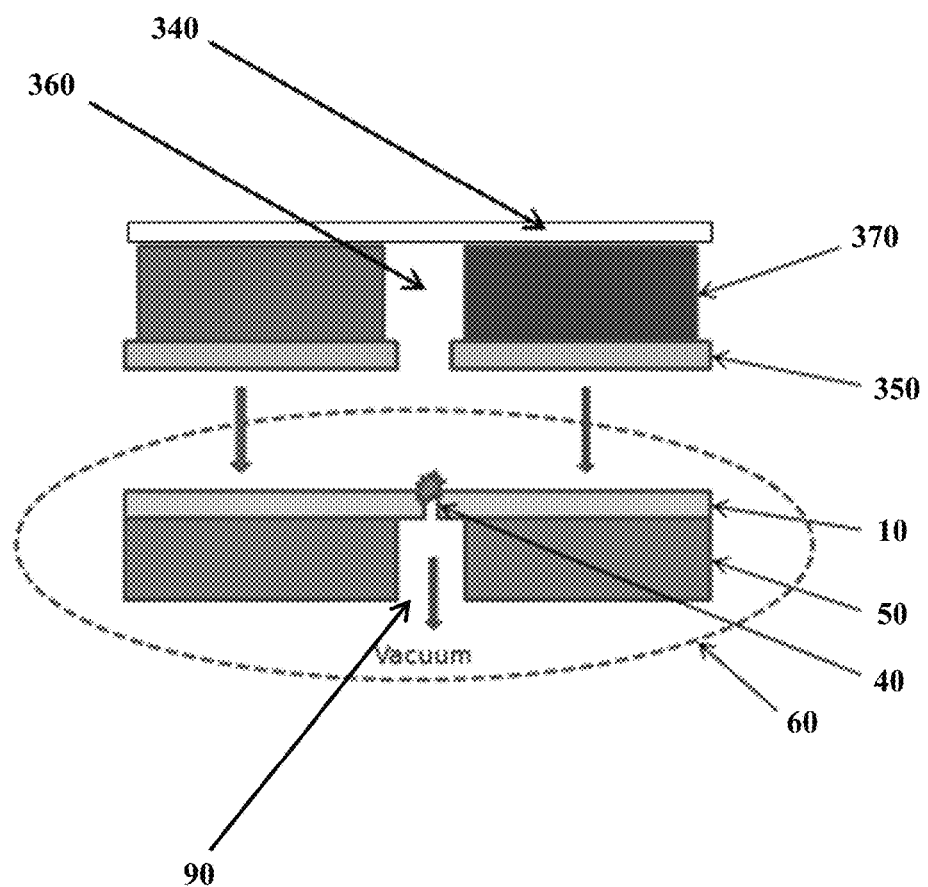
FIG. 8 show a side view of the arrangement in FIG. 7B. In particular, a multi-well chip is shown being composed of a through-hole chip (370) and a first sealing film (340) that forms a bottom and generates a well (360) in the multi-well chip. The top surface of the multi-well chip is shown with double-sided adhesive film (350) that allows the multi-well chip to attach to the polymer capture film (10) such that singe captured cells (40) align with the wells (360) of the multi-well chip. The polymer capture film (10), shown with a capture cell (40), is seated on a film support component (50) inside a housing base (60) that has a vacuum connection port (90).

Next, a chip alignment component (310) is placed on top of the polymer capture film using the chip alignment guide pin receivers (330) on the chip alignment component as shown in FIGS. 7A and 7B. A multi-well chip (320), with attach double-side adhesive film (350) (with holes formed therein), is placed inside the chip alignment component (310), on top of the polymer capture film (10). The double sided adhesive bonds the multi-well chip to the polymer capture film, and seals each well from its neighbor. FIG. 8 show a side view of the arrangement in FIG. 7. In particular, a multi-well chip is shown being composed of a through-hole chip (370) and a first sealing film (340) that forms a bottom and generates a well (360) in the multi-well chip. The top surface of the multi-well chip is shown with double-sided adhesive film (350) that allows the multi-well chip to attach to the polymer capture film (10) such that single captured cells (40) align with the wells (360) of the multi-well chip. The polymer capture film (10), shown with a capture cell (40), is seated on a film support component (50) inside a housing base (60) that has a vacuum connection port (90).

Figure 9A:
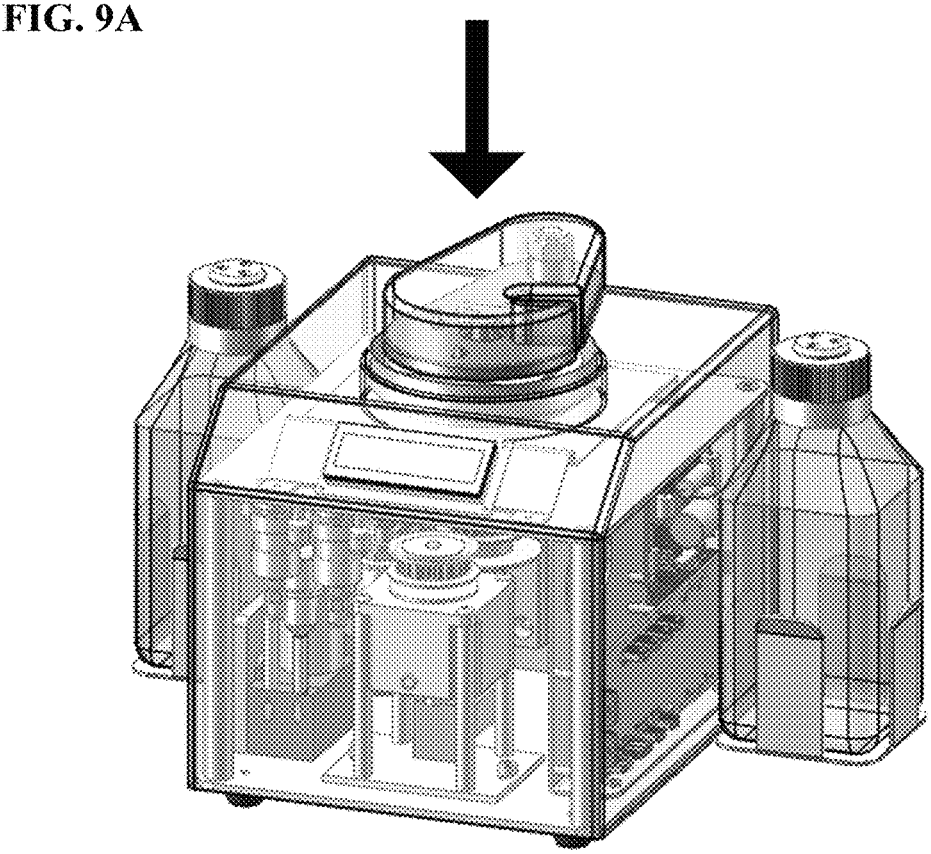
FIG. 9A shows the cell capture instrument (200) with the swing arm (210) providing force down on the multi-well chip (320).
Figure 9B:
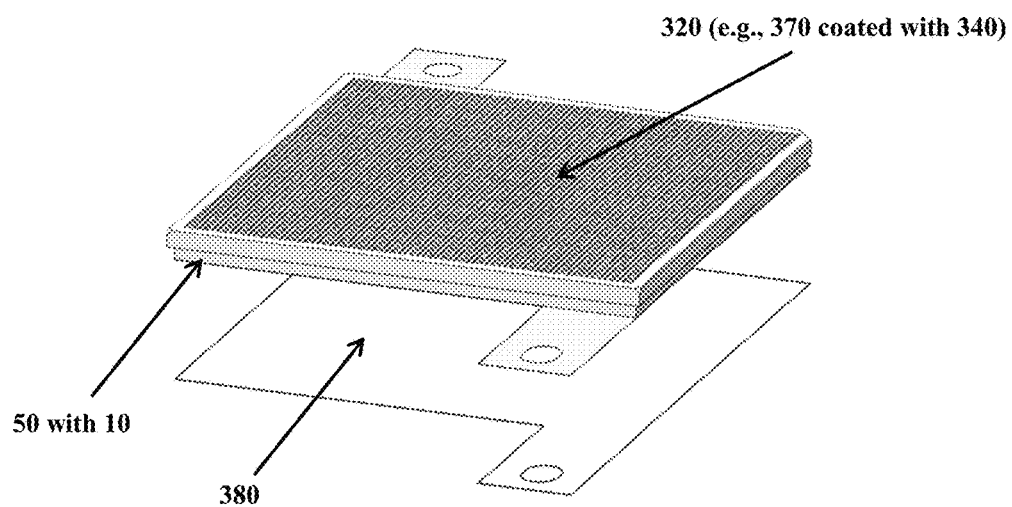
FIG. 9B shows a multi-well chip (320) component of a through-hole chip (370) coated with a first sealing film (340) to form the bottom of the chip. Below the multi-well chip (370) is a film support component (50) with the polymer capture film on top (10). A second sealing film (380) is shown below the film support component (50).

Next, as shown in FIG. 9A, the swing arm (210) comes over and down to apply pressure to the multi-well chip to seal it with the polymer capture film. The swing arm then moves up and over to allow removal of the multi-well chip/polymer capture film assembly. This assembly is then placed upside down and the bottom of the polymer capture film is blotted dry and sealed with a second sealing film (380) (e.g., PCR sealing film). In certain embodiments, to this sealed assembly, hypotonic buffer is added and the assembly is frozen at −80 C for 30 min or overnight. This assembly may be thawed at room temperature and used for any type of single cell analysis. The freeze and thaw procedure (e.g., in hypotonic solution) breaks open the cells and allows the cell lysate to be in solution in the wells of the multi-well chip. The polymer film on the top surface (e.g., a temporary sealing film) is then peeled off and the chip may be employed for any type of biological analysis. In other embodiments, the captured single cells are released from the polymer film and/or lysed with denaturants such as guanidine and urea, or with an enzyme composition.

As a result of the processing, some, most, or all of the wells of the multi-well chip now have a cell lysate from a single cell in solution. Reagents for any suitable type of assay may be added to the wells of the multi-well chip (e.g., using a multi-well dispenser, such as the one from WAFER-GEN BIOSYSTEMS). In certain embodiments, protein detection assay components (e.g., anti-body based assays) are added to the wells. In other embodiments, SNP detection assay components are added to the wells. In other embodiments, nucleic acid sequencing assay components are added to the wells. In certain embodiments, nucleic acid sequence assay components that employ barcoding for labelling individual mRNA molecules, and/or for labeling for cell/well source (e.g., if wells pooled before sequencing analysis), and/or for labeling particular multi-well chips (e.g., if wells from two or more multi-well chips are pooled prior to sequencing) are employed. Examples of such barcoding methodologies and reagents are found in Pat. Pub. US2007/0020640, Pat. Pub. 2012/0010091, U.S. Pat. Nos. 8,835,358, 8,481,292, Qiu et al. (Plant. Physiol., 133, 475-481, 2003), Parameswaran et al. (Nucleic Acids Res. 2007 October; 35(19): e130), Craig et al. reference (Nat. Methods, 2008, October, 5(10):887-893), Bontoux et al. (Lab Chip, 2008, 8:443-450), Esumi et al. (Neuro. Res., 2008, 60:439-451), Hug et al., J. Theor., Biol., 2003, 221:615-624), Sutcliffe et al. (PNAS, 97(5):1976-1981; 2000), Hollas and Schuler (Lecture Notes in Computer Science Volume 2812, 2003, pp 55-62), and WO201420127; all of which are herein incorporated by reference in their entireties, including for reaction conditions and reagents related to barcoding and sequencing of nucleic acids.

In certain embodiments, the barcode tagging and sequencing methods of WO2014201272 ("SCRB-seq" method) are employed. The necessary reagents for the SCRB-seq method (e.g., modified as necessary for small volumes) are added to the multi-chip wells, each containing a lysed single cells. Briefly, the SCRB-seq method amplifies an initial mRNA sample from a single cell in multi-well plates (as described above), where each well has a single cell. Initial cDNA synthesis uses a first primer with: i) N6 for cell/well identification, ii) N10 for particular molecule identification, iii) a poly T stretch to bind mRNA, and iv) a region that creates a region where a second template-switching primer will hybridize. The second primer is a template switching primer with a poly G 3' end, and 5' end that has iso-bases. After cDNA amplification, the tagged cDNA single cell/well samples are pooled. Then full-length cDNA synthesis occurs with two different primers, and full-length cDNA is purified. Next, a NEXTERA sequencing library is prepared using an i7 primer (adds one of 12 i7 tags to identify particular multi-well plates) and P5NEXTPT5 to add P5 tag for NEXTERA sequencing (P7 tag added to other end for NEXTERA). The library is purified on a gel, and then NEXTERA sequencing occurs. As a non-liming example, with twelve i7 plate tags, and 384 cell/well-specific barcodes, this allows total of 4,608 single cell transciptomes to be done at once. This method allows for quantification of mRNA transcripts in single cells and allows users to count the absolute number of transcript molecules/cell to remove any variables from normalization.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of isolating single cells comprising:
    a) contacting a cell suspension with a cell-isolating system, wherein said cell-isolating system comprises:
        i) a hydrophobic polymer capture film comprising a planar top surface, a bottom surface, and a plurality of individual holes extending through said polymer capture film, wherein each of said individual holes:
            A) has a top opening in said top surface of said polymer capture film,
            B) has a bottom opening in said bottom surface of said polymer capture film, and
            C) is dimensioned such that one cell, and only said one cell, from said cell suspension is captured by said top opening on said planar top surface, when negative pressure is provided to said bottom opening; and
        ii) a pneumatic device that provides said negative pressure, and
    b) incubating said cell suspension with said cell-isolating system, wherein said pneumatic device provides said negative pressure, such that at least a portion of said plurality of individual holes in said polymer capture film captures one cell from said cell suspension on said planar top surface of said polymer capture film;
c) washing said polymer capture film to remove non-captured cells to generate a captured-cell polymer film comprising a plurality of captured cells;
d) bringing together said captured-cell polymer film and a multi-well device to generate an assembly, wherein said multi-well device has a plurality of well-openings, and wherein said top openings of said plurality of individual holes of said captured-cell polymer film matches one-for-one, and aligns with, said plurality of well openings in said multi-well device; and
e) treating said assembly such that one of said captured cells, or partial contents of one of said captured cells, for each of said portion of said plurality of individual holes is transferred into the corresponding well opening of said multi-well device.

2. The method of claim 1, wherein, prior to said bringing together and said treating, at least some of said plurality of wells of said multi-well device comprises reagents such that, after said bringing together and said treating, said one captured cell, or contents of said one captured cell, are modified by said reagents.

3. The method of claim 2, wherein said reagents are selected from the group consisting of: a buffer, a lyse buffer, a polymerase, sequencing reagents, proteinase, and nucleotides.

4. The method of claim 2, further comprising sequencing nucleic acid from said captured cell or contents of said captured cell.

5. The method of claim 1, wherein said cell isolating system further comprises a porous layer comprising a porous material that allows liquid, but not cells, to pass therethrough, wherein said porous layer is in contact with said bottom surface of said polymer capture film such that said bottom opening of each of said plurality of individuals holes is covered by said porous material.

6. The method of claim 1, wherein said cell isolating system further comprises a film support component comprising a substrate with a plurality of individual holes therethrough which align one-for-one with said plurality of individual holes in said polymer capture film, wherein said film support component is in contact with, and supports, said bottom surface of said polymer capture film.

7. The method of claim 1, further comprising at least one film guide component attached to, or integral with, said polymer capture film, wherein said film guide component allows alignment of said plurality of individual holes in said polymer capture film one-for-one with wells in a multi-well device and/or holes in a polymer film support plate.

8. The method of claim 1, wherein said polymer capture film comprises at least 500 individual holes.

9. The method of claim 1, wherein said polymer capture film has a thickness between 10 µm and 50 µm, and wherein said top surface has an area between 1 $cm^2$ and 30 $cm^2$.

10. The method of claim 1, wherein each of said individual holes has a diameter of about 2-6 µm.

11. The method of claim 1, wherein said cell isolating system further comprises a film support component and a housing base, wherein said housing base contains said polymer capture film and said film support component.

12. The method of claim 11, wherein said housing base comprises at least one base feature selected from the group consisting of: a vacuum connection port, at least two guide pins for aligning said polymer capture film and said film support component, a film support plate recess, a liquid reservoir, a gasket, and at least one connection rod for connection to a housing top.

13. The method of claim 11, further comprising a housing top, wherein said housing top is connected to a housing base to enclose said polymer capture film.

14. The method of claim 13, wherein said housing top comprises at least one top feature selected from the group consisting of: an inlet port, an outlet port, a slot array, a guide pin receiver, and a connection rod receiver.

15. The method of claim 11, wherein said cell isolating system further comprises a component selected from the group consisting of: a vacuum pump that provides said negative pressure, a centrifuge motor configured to spin said housing base, a diaphragm pump, a chip alignment component, a swing arm attached to a swing arm support rod, a sample delivery component, a user interface display, and at least one waste container.

16. The method of claim 1, wherein said one captured cell is selected from the group consisting of: a platelet, a red blood cell, a neutrophil, a lymphocyte, a fibroblast, and a macrophage.

17. The method of claim 1, wherein said bringing together comprises attaching said captured-cell polymer film to said multi-well device with double-sided adhesive having holes formed therein corresponding to said well-openings in said multi-well device.

* * * * *